United States Patent
Gaffney et al.

(10) Patent No.: US 9,943,509 B2
(45) Date of Patent: Apr. 17, 2018

(54) METHODS, COMPOUNDS, AND COMPOSITIONS FOR THE TREATMENT OF MUSCULOSKELETAL DISEASES

(71) Applicant: UNIVERSITY OF SOUTHERN CALIFORNIA, Los Angeles, CA (US)

(72) Inventors: Kevin J. Gaffney, Los Angeles, CA (US); Kathleen E. Rodgers, Long Beach, CA (US); Stan G. Louie, Fullerton, CA (US); Gere S. Dizerega, San Luis Obispo, CA (US); Nicos A. Petasis, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 15/318,735

(22) PCT Filed: Jul. 17, 2015

(86) PCT No.: PCT/US2015/041020
§ 371 (c)(1),
(2) Date: Dec. 14, 2016

(87) PCT Pub. No.: WO2016/011420
PCT Pub. Date: Jan. 21, 2016

(65) Prior Publication Data
US 2017/0119748 A1    May 4, 2017

Related U.S. Application Data

(63) Continuation-in-part of application No. PCT/US2014/030071, filed on Mar. 15, 2014.

(60) Provisional application No. 62/026,006, filed on Jul. 17, 2014, provisional application No. 62/053,035, filed on Sep. 19, 2014, provisional application No. 61/802,259, filed on Mar. 15, 2013, provisional application No. 61/809,290, filed on Apr. 5, 2013.

(51) Int. Cl.
*A61K 31/4439* (2006.01)
*A61K 31/496* (2006.01)
*A61K 31/506* (2006.01)
*A61K 31/5377* (2006.01)

(52) U.S. Cl.
CPC ........ *A61K 31/4439* (2013.01); *A61K 31/496* (2013.01); *A61K 31/506* (2013.01); *A61K 31/5377* (2013.01)

(58) Field of Classification Search
None
See application file for complete search history.

(56) References Cited

U.S. PATENT DOCUMENTS

| | | |
|---|---|---|
| 6,984,660 B2 | 1/2006 | Heitsch |
| 2008/0318951 A1 | 12/2008 | Allegretti et al. |
| 2011/0009409 A1 | 1/2011 | Blair et al. |
| 2011/0178101 A1 | 7/2011 | Fatheree et al. |

FOREIGN PATENT DOCUMENTS

| | | |
|---|---|---|
| WO | 2013/078261 A1 | 5/2013 |
| WO | 2014/066964 A1 | 5/2014 |
| WO | 2014/145331 A1 | 9/2014 |
| WO | WO 2014/189634 | 11/2014 |

OTHER PUBLICATIONS

The International Search Report (ISR) for PCT/US2015/041020 dated Sep. 17, 2015, pp. 1-2.
The International Written Opinion for PCT/US2015/041020 dated Sep. 17, 2015, pp. 1-4.

*Primary Examiner* — Samantha L Shterengarts
(74) *Attorney, Agent, or Firm* — McDonnell Boehnen Hulbert & Berghoff LLP

(57) ABSTRACT

This invention provides methods, compounds and compositions for the treatment of musculoskeletal disease, muscle dysfunction, muscle-wasting disease or disorder, including hereditary myopathy, neuromuscular disease, muscular dystrophy, muscular atrophy, drug-induced myopathy, and related disease, disorder or condition that causes a decrease in muscle strength, comprising the use of heterocyclic non-peptidic compounds that act as Mas agonists and/or mimics of angiotensin 1-7.

18 Claims, 3 Drawing Sheets

METHODS, COMPOUNDS, AND COMPOSITIONS FOR THE TREATMENT OF MUSCULOSKELETAL DISEASES

RELATED APPLICATIONS

This application claims the benefit of U.S. Provisional Application No. 62/026,006, filed Jul. 17, 2014, and of U.S. Provisional Application No. 62/053,035, filed Sep. 19, 2014. The entire contents of both applications are incorporated by reference in their entirety.

This application is also related to PCT Application PCT/US14/30071, filed Mar. 15, 2014, the entire contents of which application are incorporated by reference in its entirety.

FIELD OF THE INVENTION

This invention relates to methods, compounds and compositions for the treatment of musculoskeletal diseases or disorders and related conditions (including muscular dystrophy, muscle-wasting, muscle dysfunction, and muscular injury), by using non-peptidic compounds that act as agonists of the Mas receptor and/or mimic the heptapeptide angiotensin (1-7).

BACKGROUND OF THE INVENTION

PCT Application PCT/US14/30071, filed Mar. 15, 2014, the entire contents of which is incorporated by reference in its entirety, provided novel heteroaryl non-peptidic compounds capable of modulating the Mas receptor of the Renin-Angiotensin System (also referred to herein as "RAS"), and capable of mimicking, in part or in entirety, the in vitro and in vivo activities of the endogenous Mas receptor heptapeptide ligand Asp-Arg-Val-Tyr-Ile-His-Pro, known as Angiotensin 1-7, (also referred to herein as "A(1-7)"). The present invention describes the use of these compounds for the treatment of illnesses, diseases, disorders, and conditions that cause a decrease in muscle strength (also referred to herein as musculoskeletal diseases, and as muscle dysfunction and muscle-wasting diseases).

The primary function of muscle tissue in the body is to provide a source of power. Muscle can be divided into three types: skeletal muscle, cardiac muscle, and smooth muscle. Skeletal muscle is muscle tissue capable of generating force and transferring that force to the skeleton enables breathing, movement, and posture maintenance. Cardiac muscle is muscle of the heart. Smooth muscle is muscle tissue of the arterial and bowel walls. The methods and compositions of the present invention apply primarily to skeletal muscle and, with the published efficacy of A(1-7) in pre-clinical models of cardiac dysfunction, cardiac muscle, but may additionally positively affect smooth muscles. "Skeletal muscle" and "skeletal muscles" are defined as muscles with interactions with bones, tendons, and joints.

A large number of musculoskeletal diseases have been shown to lead to a decrease in muscle strength. These include, but are not limited to, inherited or recessive myopathies (such as muscular dystrophies), muscle-wasting diseases (such as cachexia that may be the result from underlying illnesses such as acquired immunodeficiency diseases [AIDS], rheumatoid arthritis, cancer, chronic obstructive pulmonary disease [COPD], and cirrhosis), conditions of muscle atrophy or attenuation (such as sarcopenia that may be the result of aging), protracted disuse (such as paralysis, coma, extended bed rest, and ICU stay), weakness induced by surgery (such as joint replacement surgery), drug-induced myopathy and rhabdomyolysis. Muscle pathology of these diseases and conditions are mediated, in part or in whole, by a combination of immune, inflammatory, and fibrotic responses. Agents capable of blocking these responses and/or stimulating regeneration of the damaged tissue would be capable of slowing or reversing disease progression in these disorders.

The heptapeptide A(1-7) has been shown to positively affect a number of disease states prevalent in patients suffering from diseases of attenuated muscle strength. A(1-7) has been shown to block cardiac fibrogenesis and remodeling resulting in a significant reduction interstitial myocardial fibrosis and myocyte hypertrophy [Iwata et al., 2005; Grobe et al., 2007]. Recent studies extrapolated these effects to skeletal muscle and showed in both the $Dmd^{mdx}$ and Sgcd-/- mouse models of muscular dystrophy (also referred to herein as "MD"), A(1-7) reduced fibrosis, oxidative stress, and improved measures of muscle strength which was tied in $Dmd^{mdx}$ mice to inhibition of TGF-β signaling [Acuña et al., 2014; Sabharwal et al., 2012]. Finally, A(1-7) has been shown to facilitate tissue regeneration and repair through stem cell activation [Jarajapu et al., 2013; Durik et al., 2012].

Elevated levels of angiotensin II (AngII) are seen in a number of conditions that are associated with muscle atrophy or cachexia and AngII has been shown experimentally to be an atrophic factor [Sukhanov et al., 2011; Brink et al., 2001]. In mice chronically infused with AngII via minipump, co-treatment with A(1-7) has been shown in to block the atrophic effects of AngII [Cisternas et al., 2015]. In this study, histologically A(1-7) co-treatment prevented a decrease in gastrocnemius muscle fiber diameter seen with AngII infusion alone. Also, performance on the weights test [Deacon 2013] was increased with AngII/A(1-7) co-treatment compared to AngII infusion alone. Additionally, in a mouse model of endotoxin-induced sepsis, following a single injection of lipopolysaccharide (LPS), LPS-injected mice infused with A(1-7) showed a similar decrease in skeletal muscle wasting (measured by muscle fiber diameter, weights test, and isolated tetanic-specific force) compared to LPS-injected mice infused with vehicle [Morales et al., 2015].

Despite these remarkable effects in these pre-clinical models, the A(1-7) peptide and related peptidic analogs are limited in their therapeutic potential due to their high cost of manufacture and limited methods of delivery, which are typically restricted to a parenteral route of administration (e.g., subcutaneous, intramuscular, and intravenous). Therefore, there is a need for small molecule non-peptidic compounds that act as effective Mas agonists and/or as A(1-7) mimics that can be used for the treatment of musculoskeletal diseases, including muscle-wasting and muscle dysfunction diseases.

BRIEF SUMMARY OF THE INVENTION

One aspect of this invention provides methods, compounds, and compositions for the treatment of musculoskeletal diseases, including muscle dysfunction and muscle-wasting diseases or disorders and related conditions that cause a decrease in muscle strength using non-peptidic Mas agonists and/or non-peptidic mimics of A(1-7).

In one embodiment the invention provides methods, compounds, and compositions for the treatment of musculoskeletal diseases, including muscle dysfunction and muscle-wasting diseases or disorders, including hereditary myopathy, neuromuscular disease, muscular atrophy, drug-induced myopathy, or an illness, disease, disorder or condition that causes a decrease in muscle strength comprising: administering to a subject in need thereof an effective amount of a non-peptidic compound that acts as a Mas agonist and/or as a mimic of the heptapeptide A(1-7).

According to the present invention, the provided methods, compounds, and compositions involve the use of compounds and compositions provided in PCT Application PCT/US14/30071.

In one embodiment, this invention provides a method for the treatment of a subject with a musculoskeletal disease, a muscle dysfunction or muscle-wasting disease or disorder, including hereditary myopathy, neuromuscular disease, muscular dystrophy, muscular atrophy, drug-induced myopathy, or an illness, disease, disorder or condition that causes a decrease in muscle strength, comprising the administration to a subject in need thereof an effective amount of a compound having the general formula 1 including salts thereof:

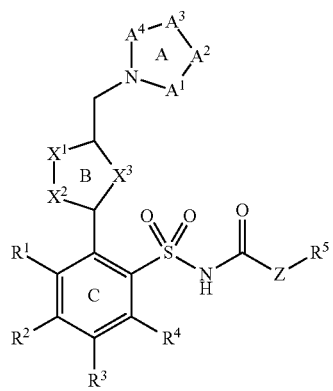

1 wherein:
ring A is a five-membered or six-membered heteroaryl or heterocyclyl ring containing either a combination of two non-adjacent nitrogen or oxygen atoms, or a combination of three or four nitrogen or oxygen atoms;
ring B is a five-membered or six-membered heteroaryl ring that contains at least one nitrogen atom;
ring C is an optionally substituted aryl ring;
$A^1$, $A^2$, $A^3$, $A^4$ are independently selected from a group consisting of =N—, —C(=O)—, —C($R^a$)=, =C($R^b$)—, —C($R^c$)($R^d$)—N($R^e$)—, —C($R^c$)($R^d$)—O—, or —[C($R^c$)($R^d$)]$_n$— with n being 1 or 2;
$X^1$—$X^2$ is ($R^6$)C—N, N—C($R^6$), N—N, N—O, O—N, N—S or S—N;
$X^3$ is ($R^7$)C=C($R^8$), O, S, or N($R^9$);
Z is O, NH or a bond to $R^5$;
$R^a$ and $R^b$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^a$ and $R^b$ can also join to form a ring of up to 6 atoms;
$R^c$ and $R^d$ are independently selected from a group consisting of hydrogen, alkyl, aryl, or heteroaryl, provided that $R^c$ and $R^d$ can also join to form a ring of up to 6 atoms;
$R^e$ is hydrogen, alkyl, aryl, heteroaryl, acyl, alkoxyacyl, aminoacyl, dialkylaminoacyl, or dialkylaminoacyl;

$R^1$, $R^3$, $R^4$, $R^6$, $R^7$, and $R^8$ are independently selected from a group consisting of hydrogen, alkyl, alkenyl, alkynyl, aryl, heteroaryl, arylmethyl, heteroarylmethyl, fluoro, chloro, bromo, iodo, cyano, hydroxy, amino, alkylamino, alkoxy, aryloxy, alkoxyalkyl, or aryloxyalkyl;
$R^2$ is alkyl, alkenyl, alkynyl, aryl, heteroaryl, arylmethyl, heteroarylmethyl, alkoxy, trifluoromethoxy, perfluoroalkoxy, aryloxy, alkoxyalkyl, or aryloxyalkyl;
$R^5$ is alkyl, aryl, heteroaryl, hydroxyalkyl, carboxyalkyl, alkoxyalkyl, or aryloxyalkyl; and
$R^9$ is hydrogen, alkyl, aryl, heteroaryl, acyl, alkoxyacyl, aminoacyl, dialkylaminoacyl, or dialkylaminoacyl.

In a second embodiment, the provided method comprises the administration to a subject in need thereof of a pharmaceutical composition comprising an effective amount of a compound having the general formula 1, as defined above, and a pharmaceutically acceptable carrier.

In a preferred embodiment, this invention provides a method for the treatment of a subject with a musculoskeletal disease, a muscle dysfunction or muscle-wasting disease or disorder, including hereditary myopathy, neuromuscular disease, muscular dystrophy, muscular atrophy, drug-induced myopathy, or an illness, disease, disorder or condition that causes a decrease in muscle strength, comprising the administration to a subject in need thereof an effective amount of a compound having the general formula 4a including salts thereof:

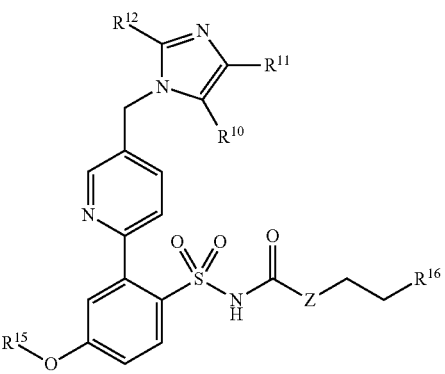

4a wherein:
Z is O or NH
$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or heteroaryl ring;
$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;
$R^{15}$ is alkyl, aryl, heteroaryl, arylmethyl, heteroarylmethyl, trifluoromethyl or pentafluoroethyl; and
$R^{16}$ is hydrogen, hydroxy, methoxy, alkoxy, alkyl, alkenyl, alkynyl, aryl, heteroaryl, amino, alkylamino, or dialkylamino.

In a further preferred embodiment, this invention provides a method for the treatment of a subject with a musculoskeletal disease, a muscle dysfunction or muscle-wasting disease or disorder, including hereditary myopathy, neuromuscular disease, muscular dystrophy, muscular atrophy, drug-induced myopathy, or an illness, disease, disorder or condition that causes a decrease in muscle strength, comprising the administration to a subject in need thereof an effective amount of a compound having the general formula 4a including salts thereof:

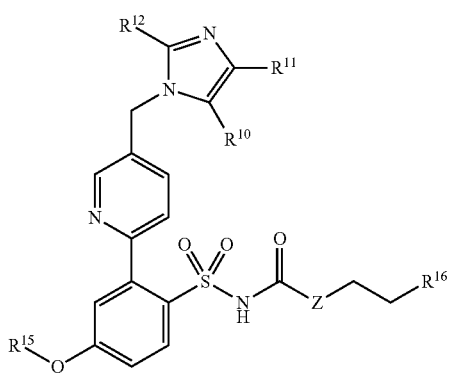

4a wherein:
Z is O or NH
$R^{10}$, $R^{11}$ and $R^{12}$ are hydrogen;
$R^{15}$ is alkyl, aryl, heteroaryl, arylmethyl, heteroarylmethyl, trifluoromethyl or pentafluoroethyl; and
$R^{16}$ is hydrogen, hydroxy, methoxy, alkoxy, alkyl, alkenyl, alkynyl, aryl, heteroaryl, amino, alkylamino, or dialkylamino.

In an exemplary embodiment, the provided method for the treatment of a subject with a musculoskeletal disease, a muscle dysfunction or muscle-wasting disease or disorder, including hereditary myopathy, neuromuscular disease, muscular dystrophy, muscular atrophy, drug-induced myopathy, or an illness, disease, disorder or condition that causes a decrease in muscle strength, comprises the administration to a subject in need thereof an effective amount of a compound having the formula 7 including salts thereof

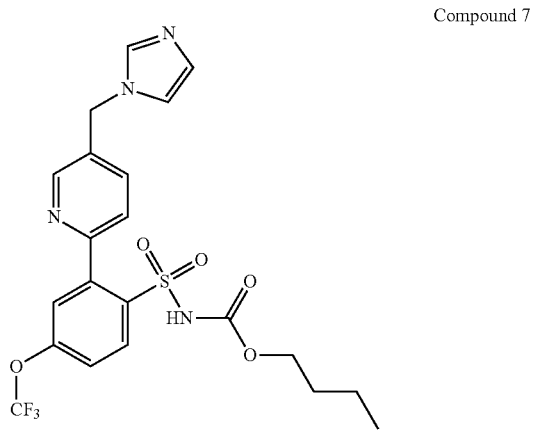 [SMILES: CCCCOC(=O)NS(=O)(=O)c1ccc(OC(F)(F)F)cc1-c1ccc(Cn2ccnc2)cn1]

Compound 7

The amount of the provided compound in each embodiment should generally be an amount effective to ameliorate at least one symptom associated with a muscle-wasting disease, or to postpone or prevent the onset of at least one symptom of the disease.

The provided compound or pharmaceutically acceptable salt thereof in each embodiment can be provided as a composition comprising the compound or pharmaceutically acceptable salt thereof and a pharmaceutically acceptable carrier suitable for oral, parenteral, or topical administration.

In one embodiment, the muscle-wasting disease is preferably a hereditary myopathy or a neuromuscular disease involving joint or skeletal deformities selected from a group consisting of: muscular dystrophy, muscle atrophy, X-linked spinal-bulbar muscular atrophy, Duchenne muscular dystrophy, Becker muscular dystrophy, limb-girdle muscular dystrophy, facioscapulhumeral muscular dystrophy, congenital muscular dystrophy, oculopharyngeal muscular dystrophy, distal muscular dystrophy, myotonic dystrophy, and Emery-Dreifuss muscular dystrophy.

In certain embodiments, the muscle-wasting disease is a hereditary myopathy selected from a group consisting of: muscular dystrophy, Duchenne muscular dystrophy, Becker muscular dystrophy, limb-girdle muscular dystrophy, facioscapulhumeral muscular dystrophy, congenital muscular dystrophy, oculopharyngeal muscular dystrophy, distal muscular dystrophy, myotonic dystrophy, and Emery-Dreifuss muscular dystrophy.

DETAILED DESCRIPTION OF THE INVENTION

Definitions

Figure 1:
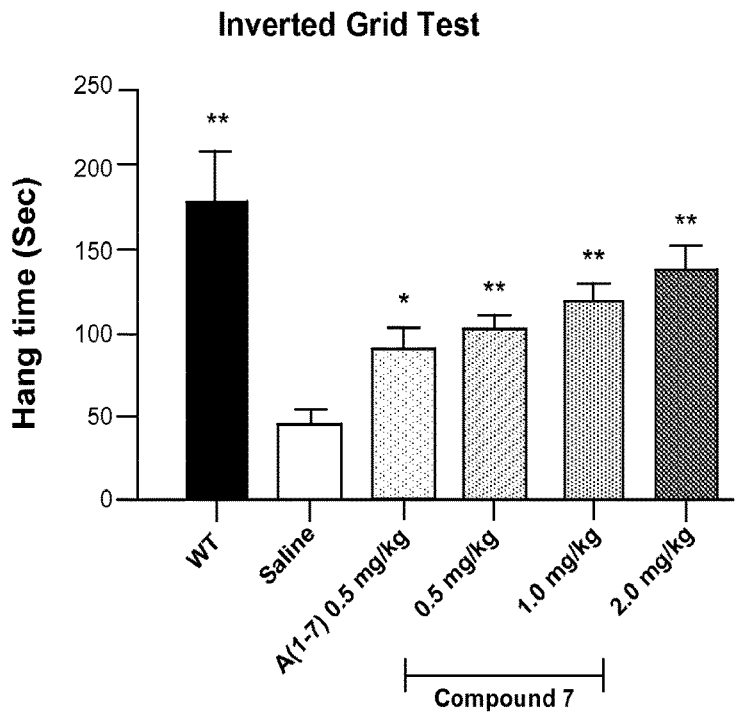
FIG. 1: Inverted Grid Test: Mouse hang times were recorded on an inverted grid test of grip strength following 8 weeks of treadmill exercise (12-15 m/min 3 times per week) and treatment. Six different subcutaneously delivered treatment groups (n=6/group) were evaluated—wild-type (WT) C57BL/10SnJ control mice plus five groups of $Dmd^{mdx}$ (C57BL/10ScSn-$Dmd^{mdx}$/J) mice: vehicle (saline/Tween 20), A(1-7) 0.5 mg/kg/day, and Compound 7 at three doses (0.5, 1.0, and 2.0 mg/kg/day). Treatment of $Dmd^{mdx}$ mice with 2.0 mg/kg/day of Compound 7 showed a significant (*=P≤0.05; **=P≤0.01, t-test) increase in hang time compared to vehicle treated $Dmd^{mdx}$ mice on the inverted grid test.

Unless defined otherwise, all technical and scientific terms used herein have the same meaning as is commonly understood by one of ordinary skill in the art. In the event that there is a plurality of definitions for a term herein, those in this section will control unless stated otherwise.

As used herein, the nomenclature alkyl, alkoxy, carbonyl, etc. is used as is generally understood by those of skill in the chemical art. As used in this specification, alkyl groups can include straight-chained, branched and cyclic alkyl radicals containing up to about 20 carbons, or 1 to 16 carbons, and are straight or branched. Exemplary alkyl groups herein include, but are not limited to, methyl, ethyl, propyl, isopropyl, isobutyl, n-butyl, sec-butyl, tert-butyl, isopentyl, neopentyl, tert-pentyl and isohexyl. As used herein, lower alkyl refer to carbon chains having from about 1 or about 2 carbons up to about 6 carbons. Suitable alkyl groups may be saturated or unsaturated. Further, an alkyl may also be substituted one or more times on one or more carbons with substituents selected from a group consisting of C1-C15 alkyl, allyl, allenyl, alkenyl, C3-C7 heterocycle, aryl, halo, hydroxy, amino, cyano, oxo, thio, alkoxy, formyl, carboxy, carboxamido, phosphoryl, phosphonate, phosphonamido, sulfonyl, alkylsulfonate, arylsulfonate, and sulfonamide. Additionally, an alkyl group may contain up to 10 heteroatoms, in certain embodiments, 1, 2, 3, 4, 5, 6, 7, 8 or 9 heteroatom substituents. Suitable heteroatoms include nitrogen, oxygen, sulfur and phosphorous.

As used herein, "cycloalkyl" refers to a mono- or multi-cyclic ring system, in certain embodiments of 3 to 10 carbon atoms, in other embodiments of 3 to 6 carbon atoms. The ring systems of the cycloalkyl group may be composed of one ring or two or more rings which may be joined together in a fused, bridged or spiro-connected fashion.

As used herein, "aryl" refers to aromatic monocyclic or multicyclic groups containing from 3 to 16 carbon atoms. As used in this specification, aryl groups are aryl radicals, which may contain up to 10 heteroatoms, in certain embodiments, 1, 2, 3 or 4 heteroatoms. An aryl group may also be optionally substituted one or more times, in certain embodiments, 1 to 3 or 4 times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

As used in this specification, a ring is defined as having up to 20 atoms that may include one or more nitrogen, oxygen, sulfur or phosphorous atoms, provided that the ring can have one or more substituents selected from a group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, phosphonate, phosphonamido, and sulfonyl, and further provided that the ring may also contain one or more fused rings, including carbocyclic, heterocyclic, aryl or heteroaryl rings.

The term "alkenyl" refers to a branched or unbranched hydrocarbon having at least one carbon-carbon double bond.

The term "alkynyl" refers to a branched or unbranched hydrocarbon having at least one carbon-carbon triple bond.

The term "carboxy" refers to a —CO$_2$H group.

The term "hydroxy" refers to an —OH group.

The term "alkoxy" refers to a group of the formula R—O— where R is an "alkyl" as defined herein.

The term "carbocycle" refers to a non-aromatic stable 3- to 8-membered carbon ring which may be saturated, mono-unsaturated or poly-unsaturated.

The term "amino" includes primary, secondary or tertiary amino groups.

The term "cyano" refers to the group —CN.

As used herein, alkenyl and alkynyl carbon chains, if not specified, contain from 2 to 20 carbons, or 2 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds.

As used herein, "heteroaryl" refers to a monocyclic or multicyclic aromatic ring system, in certain embodiments, of about 4 to about 15 members where one or more, in one embodiment 1 to 4, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, triazolyl, tetrazolyl, thienyl, pyridyl, pyrrolyl, N-methylpyrrolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "halo", "halogen" or "halide" refers to F, Cl, Br or I.

As used herein, "haloalkyl" refers to an alkyl group in which one or more of the hydrogen atoms are replaced by halogen. Such groups include, but are not limited to, chloromethyl and trifluoromethyl.

As used herein, "aryloxy" refers to RO—, in which R is aryl, including lower aryl, such as phenyl.

As used herein, "acyl" refers to a —COR group, including for example alkylcarbonyl, cycloalkylcarbonyl, arylcarbonyl, or heteroarylcarbonyls, all of which may be optionally substituted.

As used herein "subject" is an animal, typically a mammal, including human, such as a patient.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamineand other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

Compounds, Compositions and Treatment Methods

PCT Application PCT/US14/30071 provided novel non-peptidic compounds and compositions (including the synthesis thereof) capable of modulation the Mas receptor of the Renin-Angiotensin System (RAS) and/or capable of mimicking, in part or in entirety, the in vitro and in vivo activities of the endogenous Mas receptor ligand A(1-7). The present invention describes the use of compounds and compositions for the treatment of illnesses, diseases, disorders, and conditions that cause a decrease in muscle strength (also referred to herein as muscle-wasting diseases).

This invention provides methods, compounds, and compositions for the treatment of musculoskeletal diseases, including muscle dysfunction and muscle-wasting diseases or disorders, including hereditary myopathy, neuromuscular disease, muscular atrophy, drug-induced myopathy, or an illness, disease, disorder or condition that causes a decrease in muscle strength comprising: administering to a patient in need thereof an effective amount of a non-peptidic compound that acts as a Mas agonist and/or as a mimic of A(1-7). The compounds and compositions provided in PCT Application PCT/US14/30071, are able to increase muscle strength, decrease inflammation, and stimulate regeneration in muscle tissue of a rodent model of Duchenne muscular dystrophy (DMD). Therefore, the compounds and compositions described in PCT Application PCT/US14/30071 are also useful in treating muscle dysfunction and wasting associated with, but not limited to, muscular dystrophies (e.g., Duchenne muscular dystrophy, Becker muscular dystrophy, and limb-girdle muscular dystrophies), congenital myopathies, inflammatory myopathies, mitochondrial myopathies (e.g., Kearns-Sayre syndrome), inclusion body myositis (e.g., sporadic inclusion body myositis and hereditary inclusion body myopathy), metabolic myopathies, neuromuscular disease (e.g., Parkinson's disease, amyotrophic lateral sclerosis), cardiomyopathy, myocardial infarction, angina, drug-induced myopathy and rhabdomyolysis, muscular atrophy (e.g., disuse muscular atrophy, sarcopenia, and cachexia), sepsis, snakebite, and incontinence. Additionally, the methods of the invention may be used to increase muscle strength, muscle mass, or muscle endurance and decrease muscle fatigue in a subject.

Therefore, one aspect of this invention provides methods for the treatment of muscle-wasting diseases or disorders and related conditions using non-peptidic Mas agonists and/or non-peptidic mimics of A(1-7).

In one embodiment, this invention provides a method for the treatment of a subject with a musculoskeletal disease, a muscle dysfunction or muscle-wasting disease or disorder, including hereditary myopathy, neuromuscular disease, muscular dystrophy, muscular atrophy, drug-induced myopathy, or an illness, disease, disorder or condition that causes a decrease in muscle strength, comprising the administration to a subject in need thereof an effective amount of a compound having the general formula 1 including salts thereof:

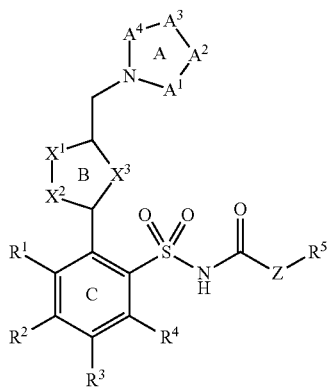

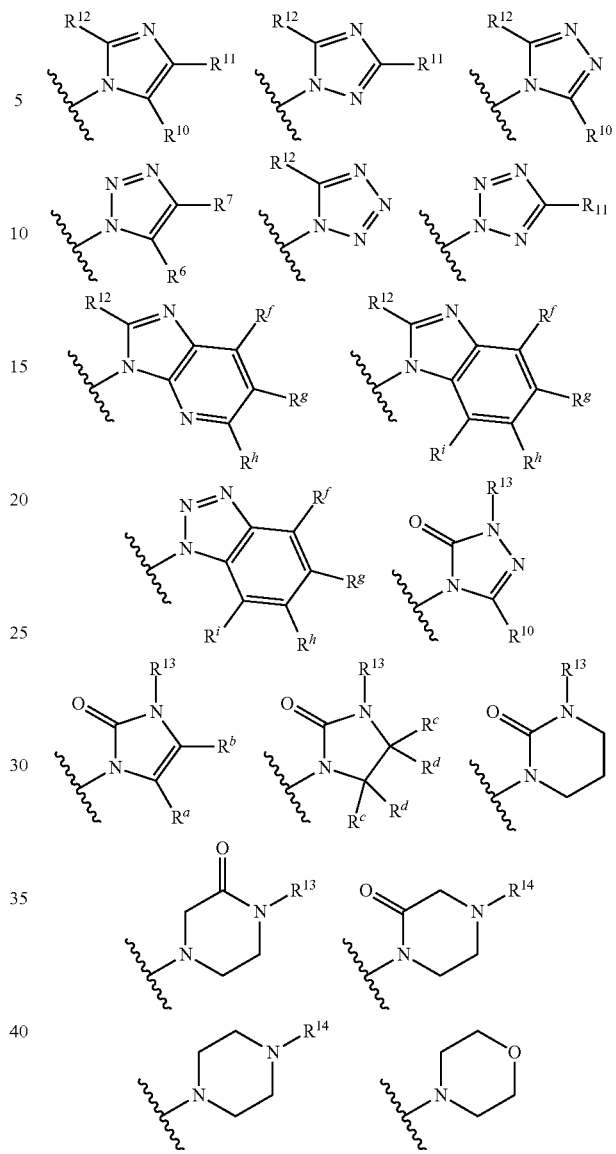

wherein:

ring A is a five-membered or six-membered heteroaryl or heterocyclyl ring containing either a combination of two non-adjacent nitrogen or oxygen atoms, or a combination of three or four nitrogen or oxygen atoms;

ring B is a five-membered or six-membered heteroaryl ring that contains at least one nitrogen atom;

ring C is an optionally substituted aryl ring;

$A^1$, $A^2$, $A^3$, $A^4$ are independently selected from a group consisting of =N—, —C(=O)—, —C($R^a$)=, =C($R^b$)—, —C($R^c$)($R^d$)—N($R^e$)—, —C($R^e$)($R^d$)—O—, or —[C($R^c$)($R^d$)]$_n$— with n being 1 or 2;

$X^1$—$X^2$ is ($R^6$)C—N, N—C($R^6$), N—N, N—O, O—N, N—S or S—N;

$X^3$ is ($R^7$)C=C($R^8$), O, S, or N($R^9$);

Z is O, NH or a bond to $R^5$;

$R^a$ and $R^b$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^a$ and $R^b$ can also join to form a ring of up to 6 atoms;

$R^c$ and $R^d$ are independently selected from a group consisting of hydrogen, alkyl, aryl, or heteroaryl, provided that $R^c$ and $R^d$ can also join to form a ring of up to 6 atoms;

$R^e$ is hydrogen, alkyl, aryl, heteroaryl, acyl, alkoxyacyl, aminoacyl, dialkylaminoacyl, or dialkylaminoacyl;

$R^1$, $R^3$, $R^4$, $R^6$, $R^7$, and $R^8$ are independently selected from a group consisting of hydrogen, alkyl, alkenyl, alkynyl, aryl, heteroaryl, arylmethyl, heteroarylmethyl, fluoro, chloro, bromo, iodo, cyano, hydroxy, amino, alkylamino, alkoxy, aryloxy, alkoxyalkyl, or aryloxyalkyl;

$R^2$ is alkyl, alkenyl, alkynyl, aryl, heteroaryl, arylmethyl, heteroarylmethyl, alkoxy, trifluoromethoxy, perfluoroalkoxy, aryloxy, alkoxyalkyl, or aryloxyalkyl;

$R^5$ is alkyl, aryl, heteroaryl, hydroxyalkyl, carboxyalkyl, alkoxyalkyl, or aryloxyalkyl; and $R^9$ is hydrogen, alkyl, aryl, heteroaryl, acyl, alkoxyacyl, aminoacyl, dialkylaminoacyl, or dialkylaminoacyl.

In some preferred embodiments, $R^2$ is trifluoromethoxy.

In other preferred embodiments, Z is O or NH.

In exemplary embodiments, ring A includes but is not limited to a ring selected from a group consisting of:

wherein:

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{13}$ is hydrogen, alkyl, aryl or heteroaryl;

$R^{14}$ is hydrogen, alkyl, aryl, heteroaryl, acyl, alkoxyacyl, aminoacyl, dialkylaminoacyl, or dialkylaminoacyl; and $R^f$, $R^g$, $R^h$, and $R^i$, are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, or aryloxyalkyl.

In other exemplary embodiments, ring B includes but is not limited to a five- or six-membered heteroaryl ring selected from a group consisting of:

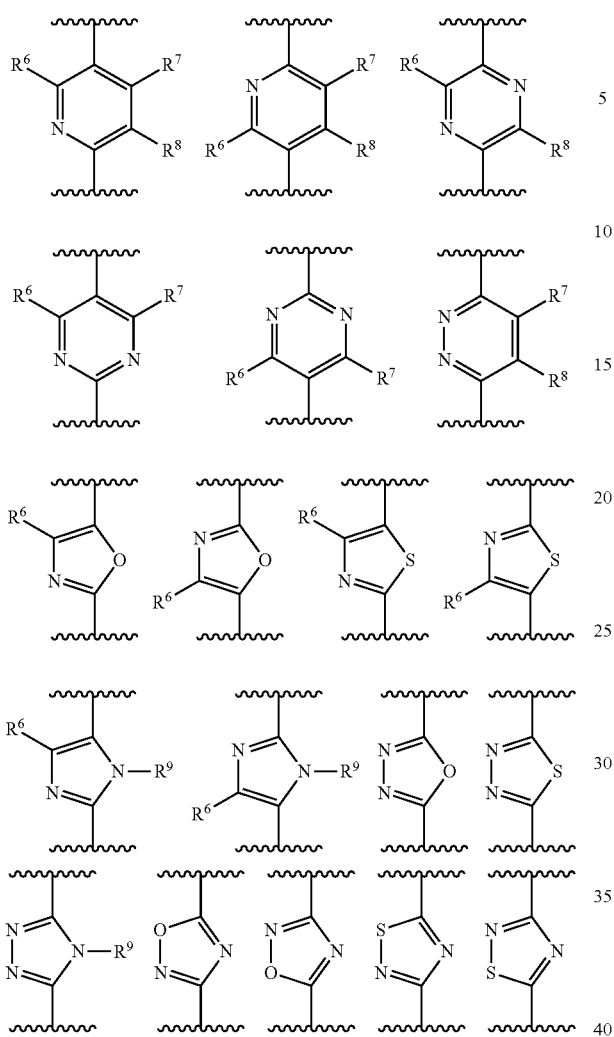
wherein groups $R^6$, $R^7$, $R^8$ and $R^9$ are defined as in general formula 1
In some exemplary embodiments, the compounds administered in connection with the methods and compositions provided herein have the general formula selected from a group consisting of:
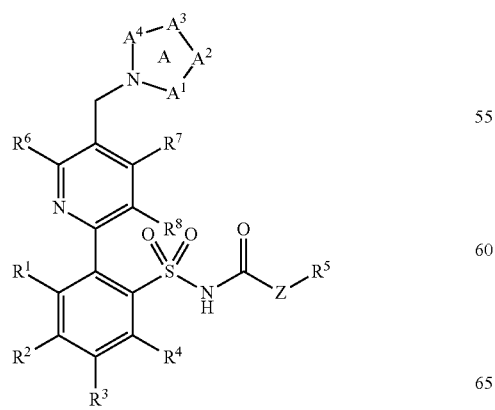
-continued
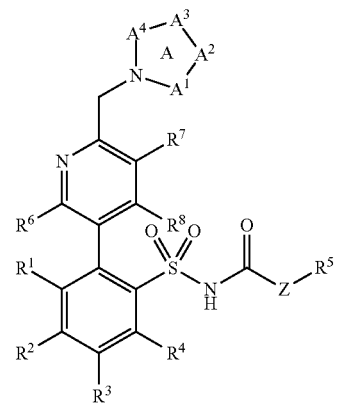
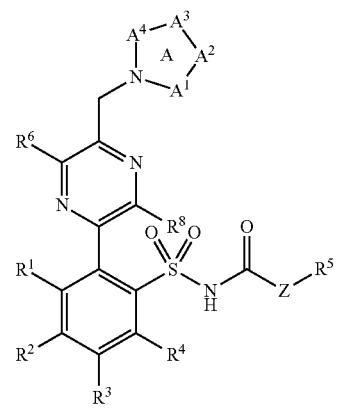
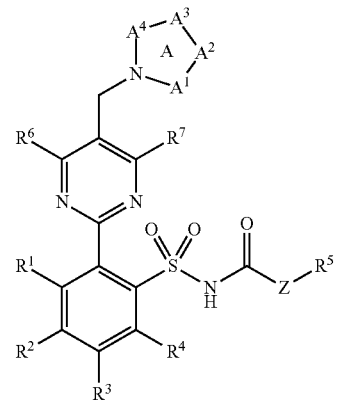
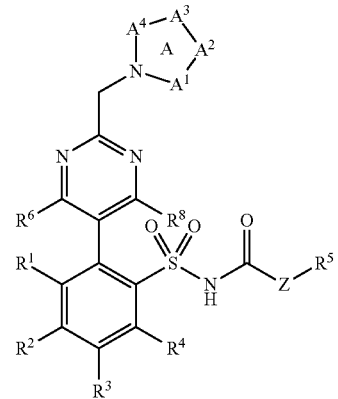

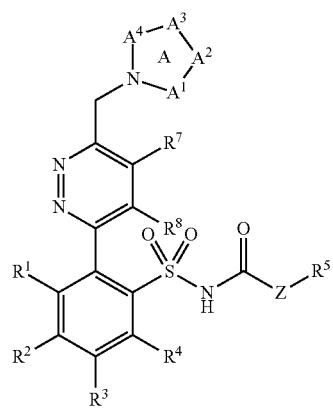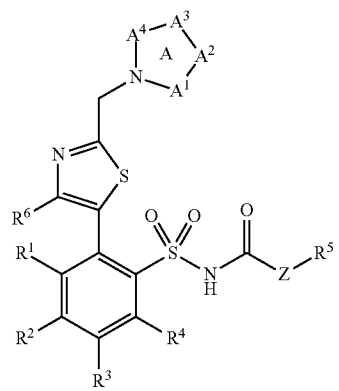

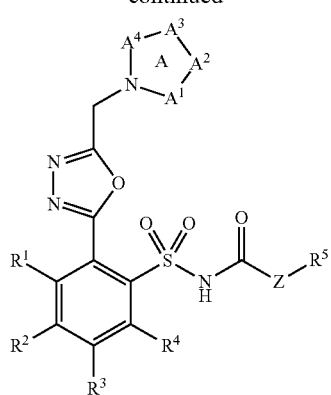
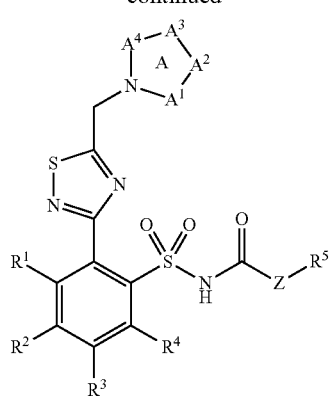
wherein groups R¹, R², R³, R⁴R⁵, R⁶, R⁷, R⁸, R⁹, A¹, A², A³, A⁴ and Z are defined as in general formula 1.
In other exemplary embodiments, the compounds have the general formula selected from a group consisting of:
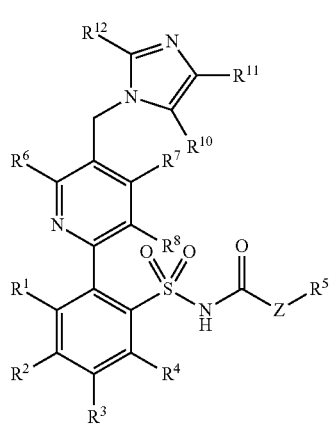

-continued
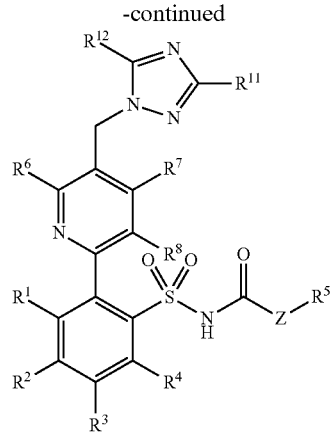
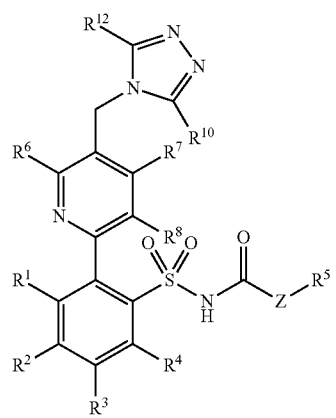
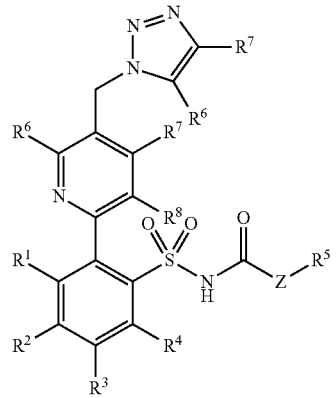
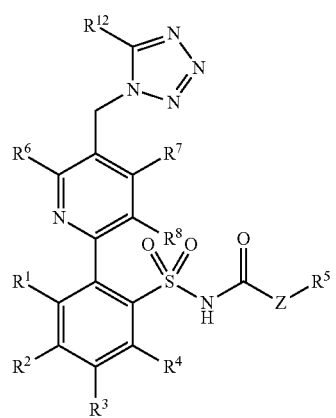
-continued
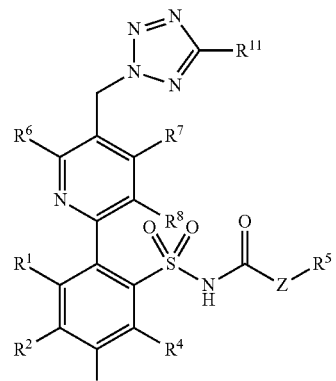
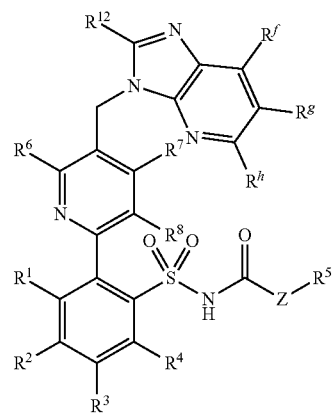
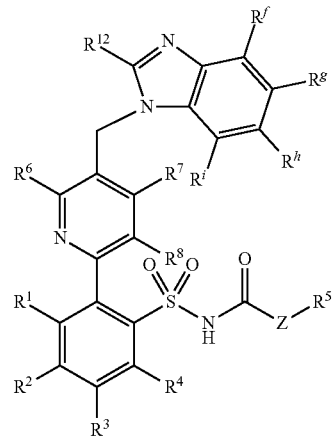
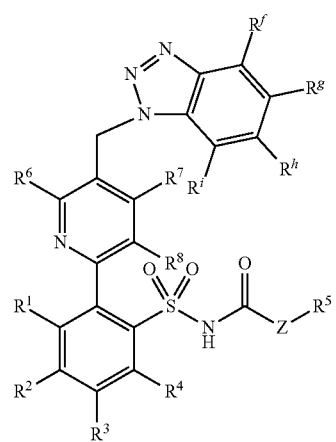

-continued
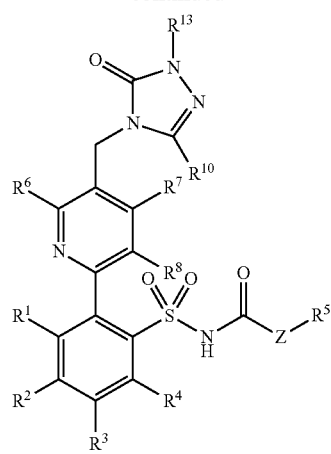
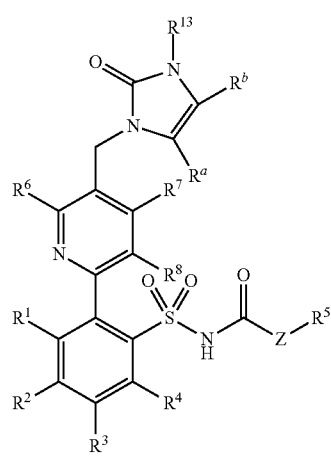
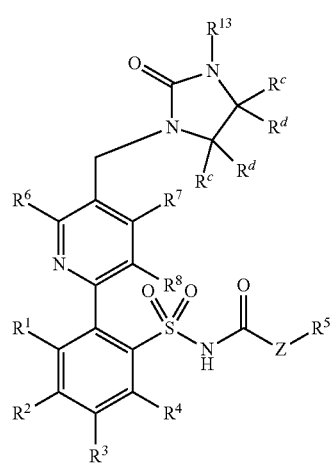
-continued
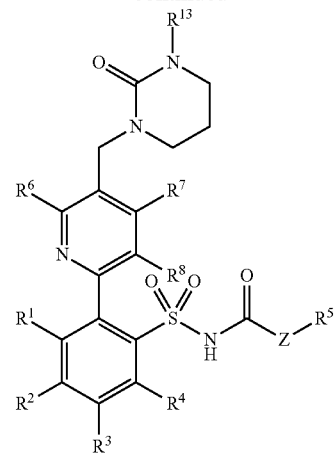
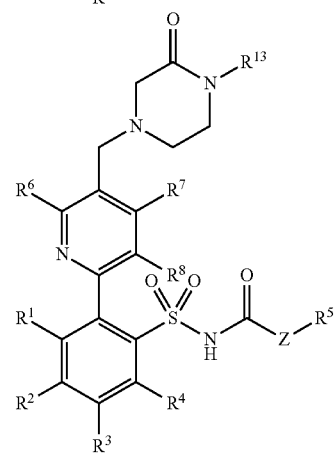
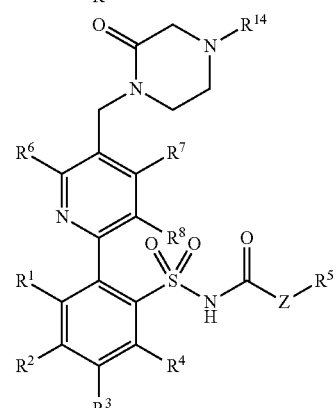
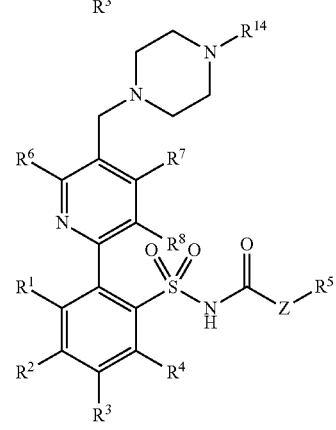

23
-continued

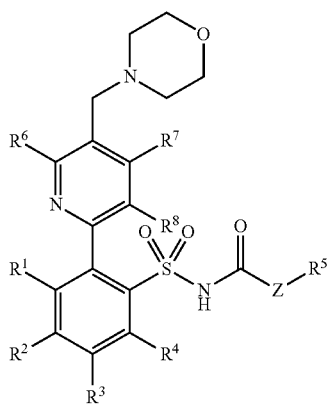

wherein:
R¹, R², R³, R⁴R⁵, R⁶, R⁷, R⁸, R⁹, $R^a$, $R^b$, $R^c$, $R^d$ and Z are defined as in general formula 1.

R¹⁰ and R¹¹ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that R¹⁰ and R¹¹ can also be joined to form a carbocyclic, heterocyclic, aryl or hetoaryl ring;

R¹² is hydrogen, alkyl, alkenyl, alkynyl, aryl, heteroaryl, halo, hydroxy, hydroxyalkyl, alkoxyalkyl, alkoxy, aryloxy, or acylamido;

R¹³ is hydrogen, alkyl, aryl or heteroaryl;

R¹⁴ is hydrogen, alkyl, aryl, heteroaryl, acyl, alkoxyacyl, aminoacyl, dialkylaminoacyl, or dialkylaminoacyl; and $R^f$, $R^g$, $R^h$, and $R^i$, are independently selected from a group consisting of hydrogen, alkyl, alkenyl, alkynyl, aryl, heteroaryl, arylmethyl, heteroarylmethyl, fluoro, bromo, iodo, hydroxy, amino, alkylamino, alkoxy, aryloxy, alkoxyalkyl, or aryloxyalkyl.

In additional exemplary embodiments, the compounds administered in connection with the methods and compositions provided herein have the general formula selected from a group consisting of:

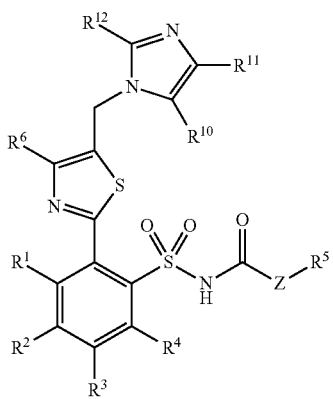

24
-continued

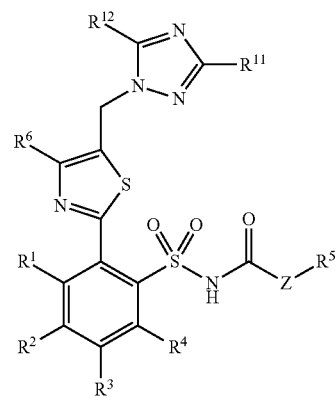

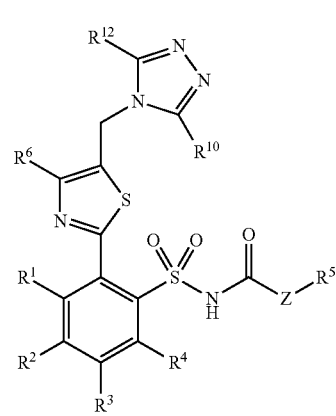

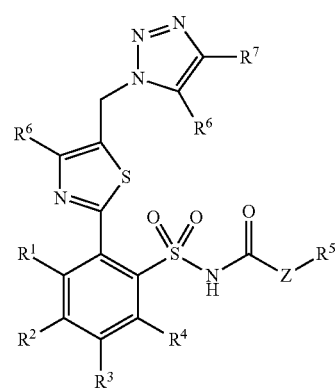

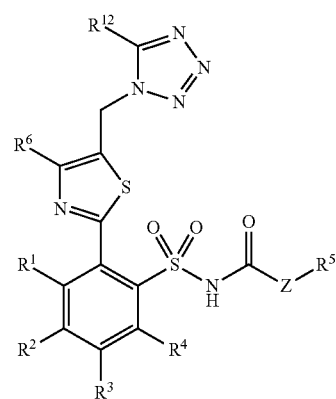

-continued
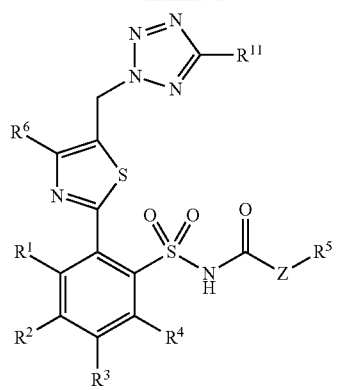
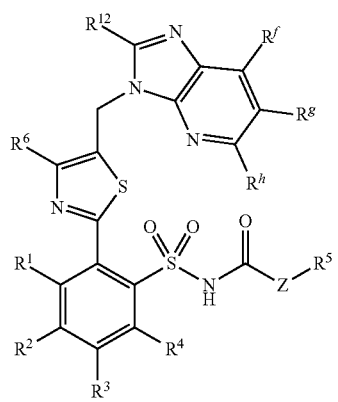
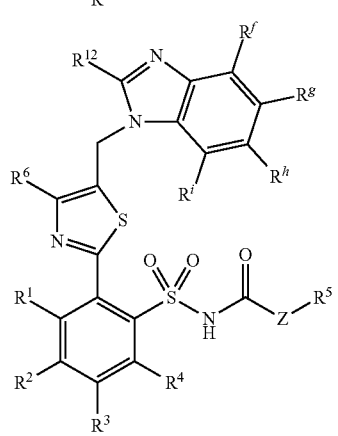
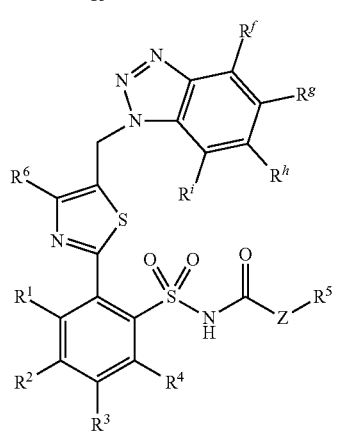
-continued
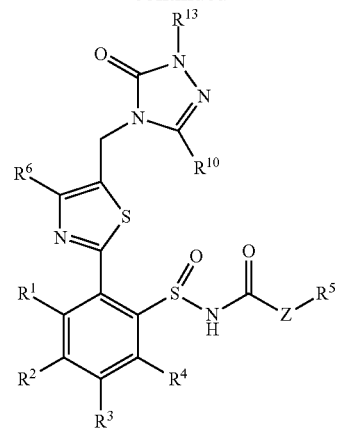
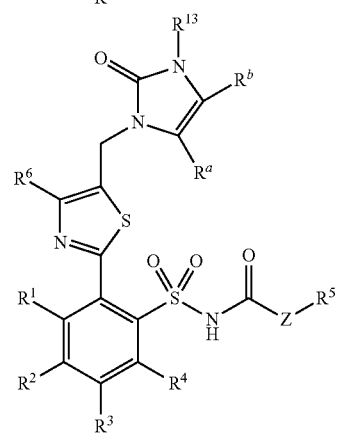
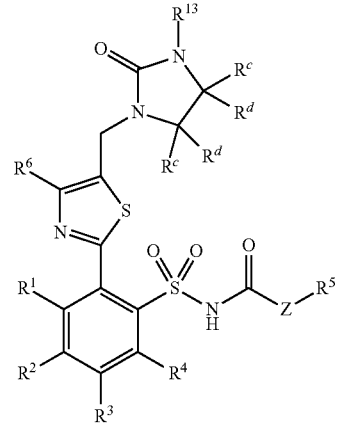
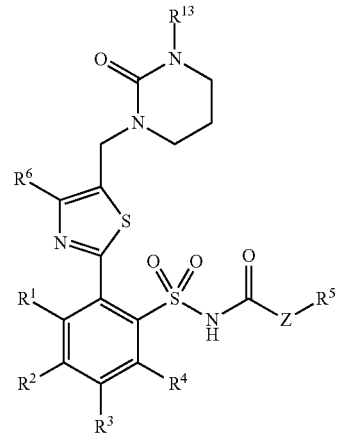

-continued

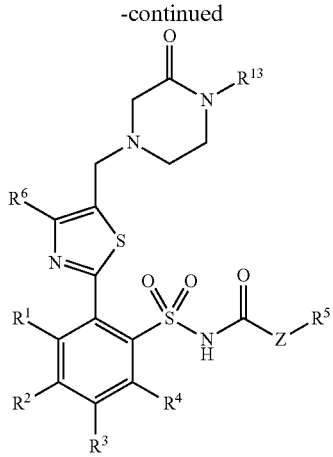

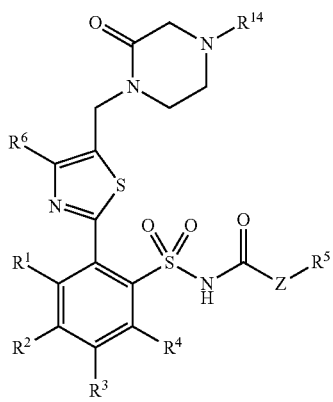

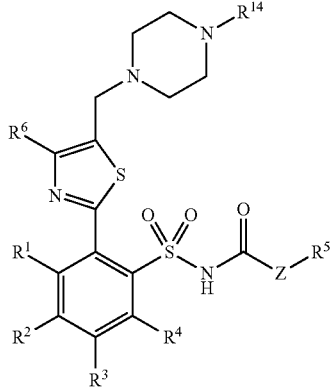

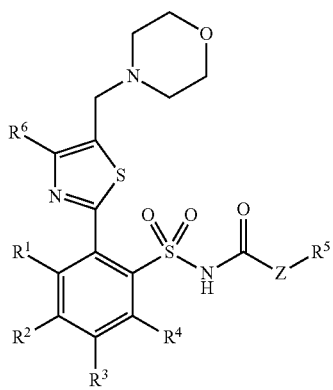

wherein:

R$^1$, R$^2$, R$^3$, R$^4$R$^5$, R$^6$, R$^7$, R$^8$, R$^9$, R$^a$, R$^b$, R$^c$, R$^d$ and Z are defined as in general formula 1.

R$^{10}$ and R$^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that R$^{10}$ and R$^{11}$ can also be joined to form a carbocyclic, heterocyclic, aryl or hetoaryl ring;

R$^{12}$ is hydrogen, alkyl, alkenyl, alkynyl, aryl, heteroaryl, halo, hydroxy, hydroxyalkyl, alkoxyalkyl, alkoxy, aryloxy, or acylamido;

R$^{13}$ is hydrogen, alkyl, aryl or heteroaryl;

R$^{14}$ is hydrogen, alkyl, aryl, heteroaryl, acyl, alkoxyacyl, aminoacyl, dialkylaminoacyl, or dialkylaminoacyl; and R$^f$, R$^g$, R$^h$, and R$^i$, are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, or aryloxyalkyl.

In some preferred embodiments, the compounds administered in connection with the methods provided herein have the general formula 2a,b or 3a,b:

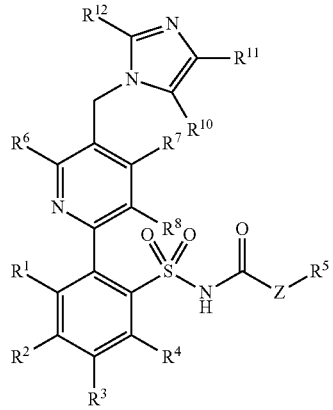

2a

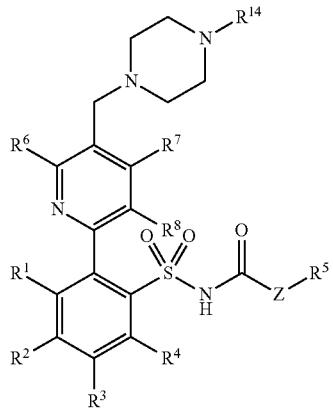

2b

-continued

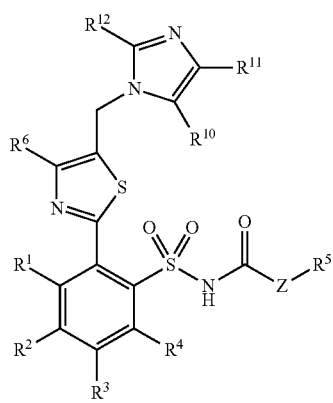

3a

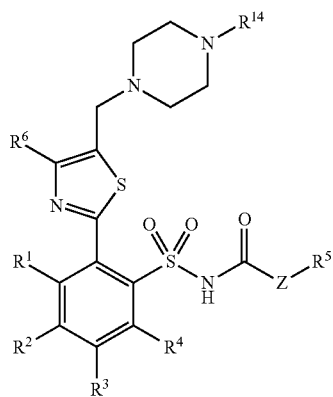

3b

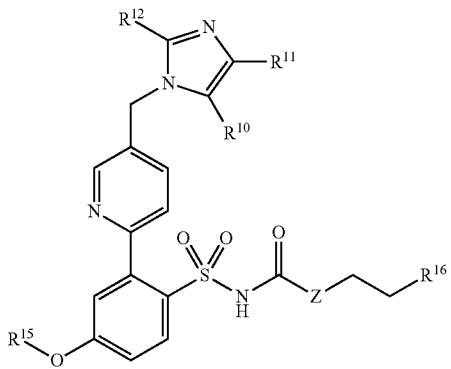

4a

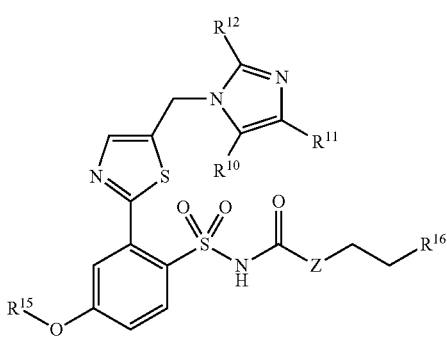

4b

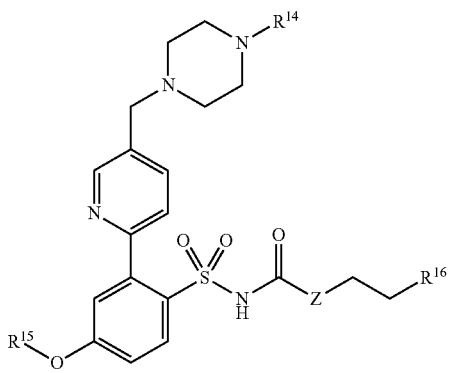

5a

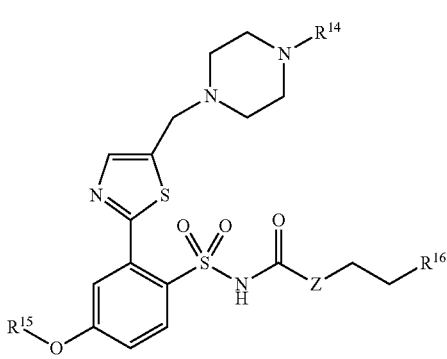

5b wherein:

$R^1$, $R^2$, $R^3$, $R^4 R^5$, $R^6$, $R^7$, $R^8$, $R^9$, $R^a$, $R^b$, $R^c$, $R^d$ and Z are defined as in general formula 1.

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{13}$ is hydrogen, alkyl, aryl or heteroaryl;

$R^{14}$ is hydrogen, alkyl, aryl, heteroaryl, acyl, alkoxyacyl, aminoacyl, dialkylaminoacyl, or dialkylaminoacyl; and $R^f$, $R^g$, $R^h$, and $R^i$, are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, or aryloxyalkyl.

In further preferred embodiments the compounds administered in connection with the methods and compositions provided herein having the general formula 4a,b, 5a,b or 6a,b:

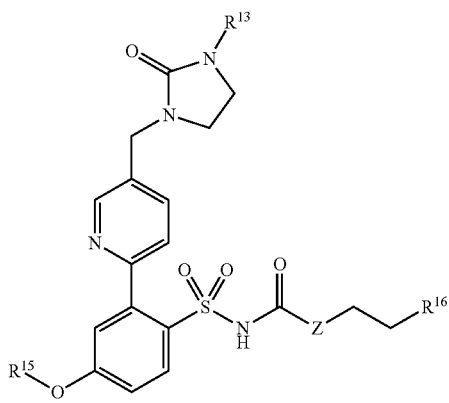

6a

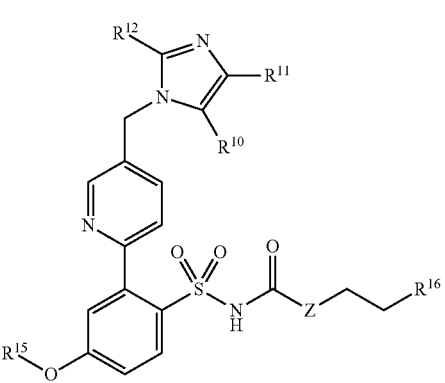

4a

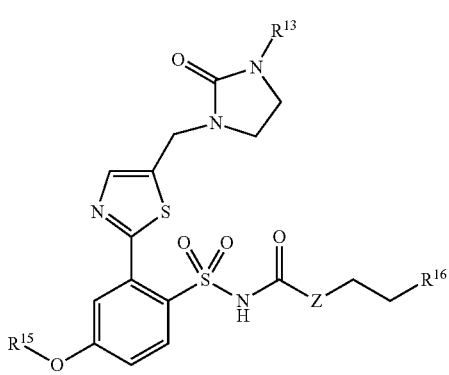

6b wherein:

R¹, R², R³, R⁴R⁵, R⁶, R⁷, R⁸, R⁹, Rᵃ, Rᵇ, Rᶜ, Rᵈ and Z are defined as in general formula 1.

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{14}$ is hydrogen, alkyl, aryl, heteroaryl, acyl, alkoxyacyl, aminoacyl, dialkylaminoacyl, or dialkylaminoacyl; and $R^{15}$ is alkyl, aryl, heteroaryl, arylmethyl, heteroarylmethyl, trifluoromethyl or pentafluoroethyl; and $R^{16}$ is hydrogen, hydroxy, methoxy, alkoxy, alkyl, alkenyl, alkynyl, aryl, heteroaryl, amino, alkylamino, or dialkylamino.

In some exemplary embodiments, the $R^{10}$, $R^{11}$ and $R^{12}$ are hydrogen, and $R^{14}$ is methyl.

In other exemplary embodiments, $R^{15}$ is trifluoromethyl and $R^{16}$ is ethyl.

Preferred embodiments of the compounds administered in connection with the methods and compositions provided herein have the general formula 4a:

wherein:

Z is O or NH $R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{15}$ is alkyl, aryl, heteroaryl, arylmethyl, heteroarylmethyl, trifluoromethyl or pentafluoroethyl; and $R^{16}$ is hydrogen, hydroxy, methoxy, alkoxy, alkyl, alkenyl, alkynyl, aryl, heteroaryl, amino, alkylamino, or dialkylamino.

In some exemplary embodiments, the $R^{10}$, $R^{11}$ and $R^{12}$ are hydrogen.

In exemplary embodiments, $R^{15}$ is trifluoromethyl and $R^{16}$ is ethyl.

Exemplary embodiments of compounds administered in connection with the methods provided herein are provided by compounds 7, 8, 9, 10, and 11:

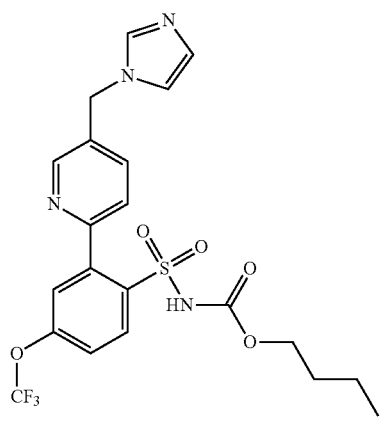

7

8

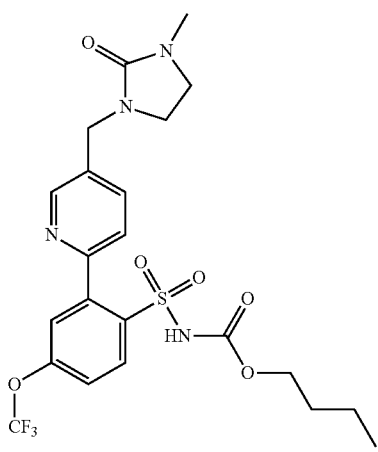

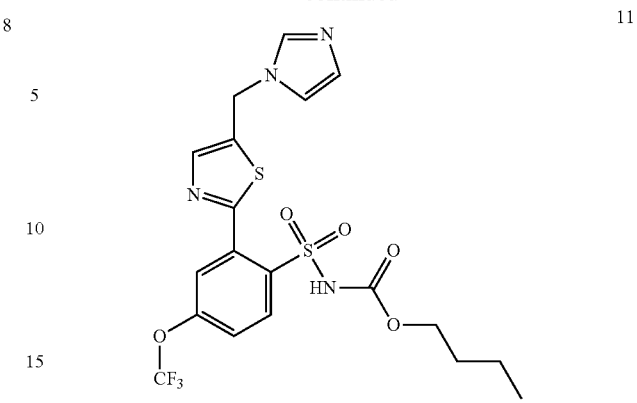

A representative exemplary embodiment of the provided methods disclosed herein comprises the administration of Compound 7 for the treatment of muscular dystrophy and related muscle-wasting diseases:

Compound 7

9

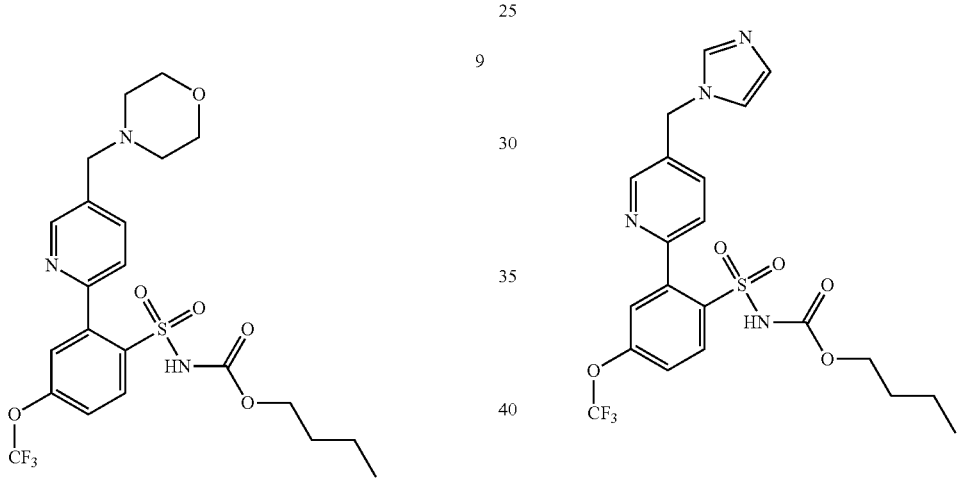

The invention further provides pharmaceutical compositions for the treatment of muscle-wasting diseases comprising a compound provided in PCT Application PCT/US14/30071 or a pharmaceutically acceptable salt, and a pharmaceutically acceptable carrier as described in PCT Application PCT/US14/30071. The provided methods and compositions are employed in oral, parenteral, or topical administration.

10

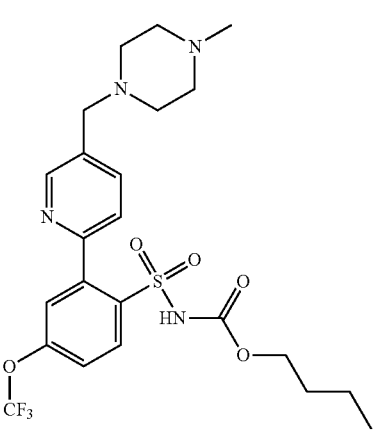

In one embodiment, the compounds and compositions described in PCT Application PCT/US14/30071 can be used to treat muscular dystrophies.

Muscular dystrophies are family of hereditary or genetic diseases. Genetic defects in genes mainly in striated muscle proteins cause weakness, usually progressive weakness, through a loss of muscle integrity and degeneration of the skeletal or voluntary muscles that control physical movement. Some muscular dystrophies also affect heart and involuntary muscles.

Some types of muscular dystrophy are associated with reduced lifespan, where the cause of mortality is often linked to dysfunction of the muscles controlling respiration. Even with improved mechanical breathing assistance, individuals with Duchenne muscular dystrophy usually succumb respiratory failure before the age of 40. Many types of muscular dystrophy can also reduce the efficiency of the heart muscle where clinical progression may lead to cardiac failure. If the disease affects muscles found in the digestive tract, this can cause swallowing difficulties which can lead to malnutrition. The symptoms and pathology of muscular dystrophy can affect individuals of all ages, where some forms clinically manifest during infancy or childhood, while other specific conditions may not appear until middle age or later. The most common form of childhood muscular dystrophy is Duchenne muscular dystrophy. The most common form of muscular dystrophy in adults is myotonic dystrophy.

Muscular dystrophy that can be treated by the compounds and compositions described in PCT Application PCT/US14/30071, including but not limited to, Duchenne muscular dystrophy, Becker muscular dystrophy, myotonic muscular dystrophy (also known as Steinert's disease), limb-girdle muscular dystrophy, sarcoglycanopathies, myotonic dystrophy, Emery-Dreifuss muscular dystrophy, congenital muscular dystrophy (e.g., Merosin-deficient congenital muscular dystrophy, Bethlem myopathy, Ullrich congenital muscular dystrophy), fascioscapulohumeral muscular dystrophy, spinal muscular dystrophy, rigid spine muscular dystrophy, distal muscular dystrophy, and oculopharyngeal muscular dystrophy.

In a preferred embodiment, the compounds and compositions described in PCT Application PCT/US14/30071, can be used to treat dystrophinopathies. Dystrophinopathies are a recessive X-linked genetic muscular dystrophy. These diseases are a consequence of a genetic mutation in deficiency or loss of functional dystrophin protein. Dystrophinopathies are a family of muscular dystrophies containing both Duchenne muscular dystrophy and Becker muscular dystrophy.

In a preferred embodiment, the compounds and compositions described in PCT Application PCT/US14/30071, can be used to treat Duchenne muscular dystrop hies.

Duchenne muscular dystrophy is one of the most common and devastating genetic diseases of childhood, affecting approximately 1 in 3500 live male births [Wilton and Fletcher 2011]. Duchenne muscular dystrophy is a severe, progressive disease which often appears between the ages of 2 and 6, leading to loss of ambulation by age 11, loss of upper arm use in the teen years, and heart and respiratory failure leading to death in the early 20's. Signs and symptoms typically first surface when the child begins to walk and may include: frequent falls, difficulty getting up from a lying or sitting position, trouble running and jumping, waddling gait, large calf muscles, and learning disabilities. Duchenne muscular dystrophy stems from a loss of functional dystrophin protein which has a structural role in linking the muscle cytoskeleton to the extracellular matrix and plays a prominent role in cell signaling and regulating muscle response to oxidative stress [Brenman et al., 1995]. The absence of dystrophin impedes the muscle's ability to tolerate conformational changes induced by contraction [Petrof et al., 1993]. The resultant muscle degeneration and inflammatory response produce a cellular environment in which adipocytes and fibroblasts proliferate and impair the regenerative capacity of muscle precursor cells [Klinger et al., 2012]. In Duchenne muscular dystrophy, the persistent breakdown of muscle cells creates an environment in such disarray that it impairs stem cells' ability to regenerated damaged tissues. After depletion of the satellite cell pool, skeletal muscle is replaced by fibrosis, leading to progressive muscle weakness [Liu et al., 2007]. Current clinical management of Duchenne muscular dystrophy includes assisted ventilation, corticosteroid administration, use of orthopedic devices to support locomotion and prevent contractures, physiotherapy, dietary changes, and corrective surgery; however, none of these treatments are capable of arresting or reversing the progression of the disease [NINDS, 2013]. In a preferred embodiment, the compounds and compositions described in PCT Application PCT/US14/30071, can be used to treat Becker muscular dystrophy. In Becker muscular dystrophy, an X-linked genetic mutation produces a partially functional dystrophin protein marked by slow, progressive loss of muscle strength in the muscles of legs and pelvis with possible cardiopulmonary affects.

In a preferred embodiment, the compounds and compositions described in PCT Application PCT/US14/30071, can be used to treat limb-girdle muscular dystrophies. Limb-girdle muscular dystrophies are a family of muscular dystrophies primarily affecting voluntary muscles of the hips and shoulder with possible cardiopulmonary affects in advanced disease. Limb-girdle muscular dystrophies that can be treated by the compounds and compositions described in PCT Application PCT/US14/30071 can be, but are not limited to, Bethlem myopathy, Calpainopathy, desmin myopathy, dysferlinopathy, myofibrillar myopathy, sarcoglycanopathies, ZASP-related myopathy, and limb-girdle muscular dystrophy 1A-H, 2A-O, and 2Q.

In a preferred embodiment, the compounds and compositions described in PCT Application PCT/US14/30071, can be used to treat dysferlinopathy. Dysferlinopathy is an autosomal recessive genetic disorder where a mutation along the dysferlin gene causes a deficiency in functional dysferlin protein. Dysferlinopathy presents clinically as Myoshi myopathy (Miyoshi muscular dystrophy-1) marked primarily by distal (e.g., hands, forearms, feet, and calves) muscle weakness and limb-girdle muscular dystrophy (limb-girdle muscular dystrophy 2B) marked by proximal (e.g., hip muscle and shoulder girdle) muscle weakness.

In a preferred embodiment, the compounds and compositions described in PCT Application PCT/US14/30071, can be used to treat myotonic muscular dystrophy. There are two types of myotonic muscular dystrophy: myotonic muscular dystrophy type 1, also known as Steinert's disease, and myotonic muscular dystrophy type 2, also known as proximal myotonic myopathy. Myotonic muscular dystrophy type 1 is the result of an expansion in CTG trinucleotide repeats DMPK gene. Myotonic muscular dystrophy type 2 is the result of an expansion in CCTG tetranucleotide repeats ZNF9 gene. Myotonic muscular dystrophy causes myotonia and muscle weakness and wasting in subjects. A method for treating myotonic dystrophy in accordance with this embodiment comprises administering to a subject in need thereof an effective amount of a compound or composition described in PCT Application PCT/US14/30071.

In a preferred embodiment, the compounds and compositions described in PCT Application PCT/US14/30071, can be used to treat congenital muscular dystrophies. Congenital muscular dystrophies are muscular dystrophies that present symptoms before age 2. A method for treating congenital muscular dystrophies in accordance with this embodiment comprises administering to a subject in need thereof an effective amount of a compound or composition described in PCT Application PCT/US14/30071.

In a preferred embodiment, the compounds and compositions described in PCT Application PCT/US14/30071, can be used to treat fascioscapulohumeral muscular dystrophy. Fascioscapulohumeral muscular dystrophy initially causes weakness in voluntary muscles of the face, shoulder blades, and upper arms and shoulder with effects on other muscles in advanced disease. Disease onset usually begins in teens or young adults. A method for treating fascioscapulohumeral muscular dystrophy in accordance with this embodiment comprises administering to a subject in need thereof an effective amount of a compound or composition described in PCT Application PCT/US14/30071.

In a preferred embodiment, the compounds and compositions described in PCT Application PCT/US14/30071, can be used to treat oculopharyngeal muscular dystrophy. Onset of oculopharyngeal muscular dystrophy initially begins with the eyelids and the throat, causing swallowing difficulty. Symptom onset is in patients is usually 40 to 60 years of age. A method for treating oculopharyngeal muscular dystrophy in accordance with this embodiment comprises administering to a subject in need thereof an effective amount of a compound or composition described in PCT Application PCT/US14/30071.

In a preferred embodiment, the compounds and compositions described in PCT Application PCT/US14/30071, can be used to treat muscle wasting associated with neuromuscular diseases. Neuromuscular diseases that can be treated by the compounds and compositions described in PCT Application PCT/US14/30071 include, but are not limited to, Parkinson's disease, amyotrophic lateral sclerosis (ALS), Huntington's disease, myasthenia gravis, centronuclear myopathy (e.g., X-linked myotubular myopathy), autoimmune neurodegenerative diseases (e.g., Guillain Barre syndrome, chronic inflammatory demyelinating polyneuropathy, Lambert-Eaton myasthenia syndrome), Creutzfeldt-Jakob disease, and stroke. A method for treating muscle wasting associated with neuromuscular diseases in accordance with this embodiment comprises administering to a subject in need thereof an effective amount of a compound or composition described in PCT Application PCT/US14/30071.

In certain embodiments, the methods of the present invention are used to treat or prevent drug-induced myopathies in subjects receiving treatments that can cause rhabdomyolysis. Rhabdomyolysis can be caused by genetic diseases, traumatic injuries, illnesses (e.g., sepsis, seizures, dehydration, electrolyte imbalance) and drug-induced. Drugs that can cause muscle breakdown that can be treated by the compounds and compositions described in PCT Application PCT/US14/30071, include HMG-CoA reductase inhibitors or "statin" (e.g., atorvastatin, rosuvastatin, lovastatin simvastatin, pravastatin, pitavastatin, cerivastatin, or fluvastatin), lipid lowering agents or "fibrates" (e.g., gemfibrozil, bezafibrate, fenofibrate, and ciprofibrate), illicit drugs (e.g., heroin, cocaine, amphetamines, methadone, D-lysergic acid diethylamide (LSD)), selective serotonin reuptake inhibitors (e.g., sertraline, citalopram, escitalopram, paroxetine, fluoxetine, fluvoxamine), multi-kinase inhibitors (e.g., imatinib, dasatinib, nilotinib, sorafenib, sunitinib, and lapatinib) and antihistamines. A method for treating or preventing drug-induced myopathies in subjects receiving treatments that can cause rhabdomyolysis in accordance with this embodiment comprises administering to a subject in need thereof an effective amount of a compound or composition described in PCT Application PCT/US14/30071.

In one embodiment, the compounds and compositions described in PCT Application PCT/US14/30071, can be used to treat muscular atrophy. Muscular atrophy is a general term used to describe a condition marked by the wasting or loss muscle tissue resulting from a variety of diseases, disorders, other conditions, or events. Muscle atrophies that can be treated by the compounds and compositions described in PCT Application PCT/US14/30071 can be the result of, but are not limited to, protracted immobilization resulting from recovery from severe burns, major joint replacement surgery, neuropathic pain, peripheral neuropathy, necrotizing vasculitis, zero gravity environment (e.g., astronauts and cosmonauts), extended hospitalization, degenerative disease (e.g., amyotrophic lateral sclerosis) and organ transplant as well as spinal cord injury, chronic hemodialysis, and stroke. A method for treating muscular atrophy in accordance with this embodiment comprises administering to a subject in need thereof an effective amount of a compound or composition described in PCT Application PCT/US14/30071.

In a preferred embodiment, the compounds and compositions described in PCT Application PCT/US14/30071, can be used to treat disuse muscular atrophy. Disuse muscular atrophy is a condition marked by the wasting or loss muscle tissue resulting from long periods of inactivity. Disuse muscular atrophy that can be treated by the compounds and compositions described in PCT Application PCT/US14/30071 can be result of, but are not limited to, protracted immobilization resulting from recovery from severe burns, major joint replacement surgery, neuropathic pain, zero gravity environment (e.g., astronauts and cosmonauts), extended hospitalization, anorexia, and organ transplant as well as spinal cord injury, chronic hemodialysis, and stroke. A method for treating disuse muscular atrophy in accordance with this embodiment comprises administering to a subject in need thereof an effective amount of a compound or composition described in PCT Application PCT/US14/30071.

In one embodiment, the compounds and compositions described in PCT Application PCT/US14/30071, can be used to treat age-related muscular atrophy. Age-related muscular atrophy is a condition marked by the wasting or loss muscle tissue and the replacement of muscle tissue with fibrosis tissue as the subject ages. A method for treating age-related muscular atrophy in accordance with this embodiment comprises administering to a subject in need thereof an effective amount of a compound or composition described in PCT Application PCT/US14/30071.

In one embodiment, the compounds and compositions described in PCT Application PCT/US14/30071, can be used to treat sarcopenia. Sarcopenia is a condition marked by the wasting or loss muscle tissue and the replacement of muscle tissue with fibrosis tissue as the subject ages. A method for treating sarcopenia in accordance with this embodiment comprises administering to a subject in need thereof an effective amount of a compound or composition described in PCT Application PCT/US14/30071.

In one embodiment, the compounds and compositions described in PCT Application PCT/US14/30071, can be used to treat the muscle wasting in cachexia. Cachexia is the marked loss of muscle and adipose tissue as a result of chronic disease. The muscle wasting component of cachexia that can be treated by the compounds and compositions described in PCT Application PCT/US14/30071 can be result of, but are not limited to, cancer, multiple sclerosis, tuberculosis, acquired immune deficiency syndrome, human immunodeficiency virus, malnutrition, Parkinson's disease, emphysema, heart failure, motor neuron disease, cystic fibrosis, dementia, sarcopenia, chronic obstructive pulmonary disease, kidney disease, and kidney failure. A method for treating muscle wasting in cachexia in accordance with this embodiment comprises administering to a subject in need thereof an effective amount of a compound or composition described in PCT Application PCT/US14/30071.

In one embodiment, the compounds and compositions described in PCT Application PCT/US14/30071, can be used to treat muscle wasting resulting from viral infections (e.g., HIV, Epstein-Barr virus), bacterial infections (e.g., mycobacteria and *rickettsia*), post-polio syndrome, and parasitic infection (e.g., trypanosomes and *schistosoma*). A method in accordance with this embodiment comprises administering to a subject in need thereof an effective amount of a compound or composition described in PCT Application PCT/US14/30071.

The subject in need of the treatments and methods of the present invention are primarily mammals, including humans, suffering from muscle wasting, but they may also be healthy individuals to increase athletic performance and musculature (e.g., body building), and prophylactically by manual workers. As used herein, the term "treat" or "treatment" means any manner in which one or more of the symptoms of a disease or disorder are ameliorated or otherwise beneficially altered. Treatment also encompasses any pharmaceutical use of the compositions herein, such as use for treating a disease as provided herein.

The methods of this invention include the administration to a subject an effective amount of the compounds or compositions described in PCT Application PCT/US14/30071 or a pharmaceutically acceptable salt thereof to treat dysfunction, reduce fatigue, and increase strength in the affected muscles in the treated subject. An "effective amount" of a compound or composition is an amount sufficient to carry out a specifically stated purpose.

Subject identified for as candidates for treatments containing the compounds and compositions described in PCT Application PCT/US14/30071 can be done by one skilled in the art. The symptoms of muscular dysfunction conditions and disorders include, but are not limited to, frequent falling, muscle wasting, progressive muscle wasting, waddling gait, scoliosis, trouble running and jumping, difficulty lifting objects, myotonia, drooping eyelids, large calf muscles, muscle hypertrophy, muscle hypotrophy, respiratory difficulty, inability to walk, learning disabilities, poor balance, difficulty getting up from a lying or sitting position, use of the Gower's maneuver to stand, and reduced endurance. Diagnosis of muscular dysfunction conditions and disorders in mammals to receive treatment containing an effective amount of a compound described in PCT Application PCT/US14/30071, or a pharmaceutically acceptable salt thereof, by, but not limited to, patient history, family history, medication history, risk factors, physical examination, blood testing, electromyography, muscle biopsy, genetic testing of patient or parent(s), or any other evidence deem suitable by one skilled in the art.

The therapeutic efficacy of the method of the present invention, using a compound described in PCT Application PCT/US14/30071 or a pharmaceutically acceptable salt thereof, used as a standalone therapy or in combination with other interventions, can be evaluated by, but not limited to, muscle strength, pulmonary function, physical examination, range of motion, blood testing (e.g., blood creatine kinase levels), electromyography, ischemic forearm test, histopathology (e.g., muscle biopsy), direct or estimation of $VO_2$ max, functional outcomes questionnaire, or any other evaluative technique deemed suitable by one skilled in the art. Measures of muscle strength or function may be determined by, but are not limited to, dynamometic measures, stair test, sit-to-stand repetition test, 6 minute walk test, timed 10 walk or run, and cardiac function. "Dyanometric measure" and "dyanometric measures" may include, but are not limited to, force of hip, ankle, knee, and elbow flexion, knee extension, and grip, "Cardiac function" measures may include, but are not limited to, left ventricular ejection fraction, systolic and diastolic left ventricular volumes, and late gadolinium enhancement (LGE) as measured by, but not limited to, MRI and Echocardiography. "Pulmonary function" measures may include, but are not limited to peak expiratory flow rate, expiratory pressures, forced expiratory volume in 1 second, forced vital capacity, and maximal inspiratory.

The compounds described in PCT Application PCT/US14/30071, or their pharmaceutically acceptable salts thereof, may be used to treat or prevent muscle dysfunction, or improve muscle function, in combination with interventions such as, but not limited to, surgical techniques, behavioral therapies, physical therapy, exercise, glucocorticoids, immune modulators, anti-inflammatory agents, anti-estrogen agents, amino acid supplements, protein supplements, herbal supplements, vitamins, minerals, and multi-vitamins.

The invention will be further described in the following examples, which are illustrative only, and which are not intended to limit the scope of the invention described in the claims.

EXAMPLES

Example 1

Effect of administration of a non-peptidic small molecule Mas agonist ("Mas agonist"), Compound 7, once daily by subcutaneous injection for 10 weeks in comparison with Angiotensin (1-7), a peptide shown in the literature to improve outcomes in mdx mice.

Test System:
Species: DMD Mutant: Male $Dmd^{mdx}$
Controls: C57BL/10ScSnJ; 10 weeks old; N=6/group
Parameters Measured: Inverted Grid Test; Forelimb strength test;
Quantitation of MSC in bone marrow; Muscle histology
Test Articles: (1) Compound 7 in Tween in saline (0.5, 1 or 2 mg/kg/day); (2) A(1-7) in saline (0.5 mg/kg/day)

Mice: The X-linked dystrophin gene (Dmd) is highly expressed in muscle cells. $Dmd^{mdx}$ mice, like human Duchenne muscular dystrophy (DMD) patients, do not produce the protein dystrophin. $Dmd^{mdx}$ mutant mice have muscles that are less elastic and, as a result, are more easily injured by lengthening-activation.

Materials: The Mas agonist used was the non-peptidic small molecule butyl ((2-(5-((1H-imidazol-1-yl)methyl) pyridin-2-yl)-4-(trifluoromethoxy)phenyl)sulfonyl)carbamate (Compound 7), which was synthesized as disclosed in the pending patent application PCT/US14/30071. A(1-7) was purchased from BACHEM.

Methods: 10 weeks old male $Dmd^{mdx}$ mice were exercised at 12-15 m/min for 30 min 3 times a week for 10 weeks. The absence of dystrophin in $Dmd^{mdx}$ mice produces a vastly different phenotype than dystrophin deficiency in humans does [De Luca et al., 2003]. With treadmill exercise, a more Duchenne-like weakness is expressed exhibiting a characteristic temporal pattern of progressive weakness [De Luca et al., 2003]. In this study, 10 weeks of exercise during treatment was used. There were six different treatment groups—Wild Type plus five groups of $Dmd^{mdx}$ mice: Vehicle, Compound 7 0.5 mg/kg/day, Compound 7 1 mg/kg/day, Compound 7 2.0 mg/kg/day, and 0.5 mg/kg/day Angiotensin (1-7).

Inverted grid test: Inverted grid test was done in order to test the muscle strength of mice.

The basic aim of the inverted grid test is to determine the amount of time that the mice could hold on to the wire mesh when it is inverted. The hang time of the mice can be used to gauge their strength relative to one another. In the inverted grid exhaustion test, the mice were acclimatized in the behavior room for at least an hour before the test was begun. To start, a mouse was placed in the center of the wire mesh box and repositioned if it moved into the corner. The box was inverted gently but quickly. If the mouse fell, the mouse was rested for at least 30 seconds before being retested on the same wire mesh. Three attempts were made in such a case, irrespective whether the mouse moved in the $2^{nd}$ attempt. Of the three attempts, the best among the three were considered for scoring.

Forelegs grip strength test: A second test to assess muscle strength, the weights test of grip strength, was also conducted [Deacon, 2013]. The weights were lined up on the bench in ascending order. There were total six weights, each with an increasing number of metal links attached to a ball of wire mesh ranging from 20 g to 83 g.

The first mouse to be tested was lifted by its tail and held for 5 seconds just above the weight. The mouse was then lowered slowly until it grabbed the weight with its forelegs. (Mice have inherent tendency of to grab things) The mouse was raised up so that it would be lifting the weight off the bench. The mouse needed to hold the weight off the bench for 3 seconds to be successful. After the first mouse was tested, the test was repeated with the second and the third mouse of the three-mouse cage. Once all three mice were successful at lifting a weight, the first mouse was picked up again and tested with the next higher weight.

Each mouse had 3 attempts to lift each weight for 3 seconds. At the second attempt, the mouse was held for 10 seconds above the weight before being lowered to grab on to the weight. This was done in order to motivate the mouse. At the third attempt the mouse was held by its tail for 15 seconds before it was lowered to lift the weight.

If the mouse is unsuccessful at lifting a particular weight for 3 seconds in all 3 attempts then the weight lower than the current weight was recorded as the last successful weight lifted by the mouse. The number of seconds (0 or 1 or 2) was recorded for the highest weight the mouse can lift.

The following formula was used to calculate the score: Number of links a mouse can lift for 3 seconds×3+number of seconds for which the mouse lifted higher weight Necropsy: At the conclusion of the 9-week observation period (19 weeks of age), all animals were euthanized, and tissue samples and bone marrow (below) were collected. The tissues collected were the diaphragm, gastrocnemius muscle, soleus muscle, tibialis anterior muscle, plantaris muscle and heart. The gastrocnemius muscle, soleus muscle, tibialis anterior muscle, plantaris muscle from the left leg as well as the diaphragm and heart were fixed in formalin and stored in 70% EtOH for hematoxylin and eosin (H&E) staining.

Histological Evaluation of the Diaphragm: The diaphragm was embedded in paraffin, sectioned and stained by H & E (hematoxylin and eosin). The parameters were assessed include (1) the number of regenerating fibers as defined by basophilic fibers; (2) number of degenerating fibers and the number of inflammatory loci (clusters of 10 or more inflammatory cells). Five random 40× fields per diaphragm were evaluated.

Bone Marrow Harvest: The bone marrow was harvested from the femurs of mice by flushing with phosphate buffered saline (PBS), pH 7.4, containing 2% fetal bovine serum (FBS) with a 21-gauge needle. The eluant from the flushing was centrifuged and the pellet was resuspended at $5\times10^7$ nucleated cells/ml in PBS containing 2% FBS and 5% normal rat serum.

Mesenchymal stem cells (MSC) counts: The bone marrow cells were cultured to assess the number of MSCs by a CFU-F assay. $5\times10^5$ cells were diluted into Mesencult medium (Stem Cell Technologies, Vancouver, BC, Canada) in a volume of 2 mL and placed in each well of a 24 well plate. The cultures were then incubated at 37° C. in a humidified atmosphere of 5% $CO_2$ in air. At day 8, the number of progenitor colonies formed was enumerated under phase contrast microscopy.

Figure 2:
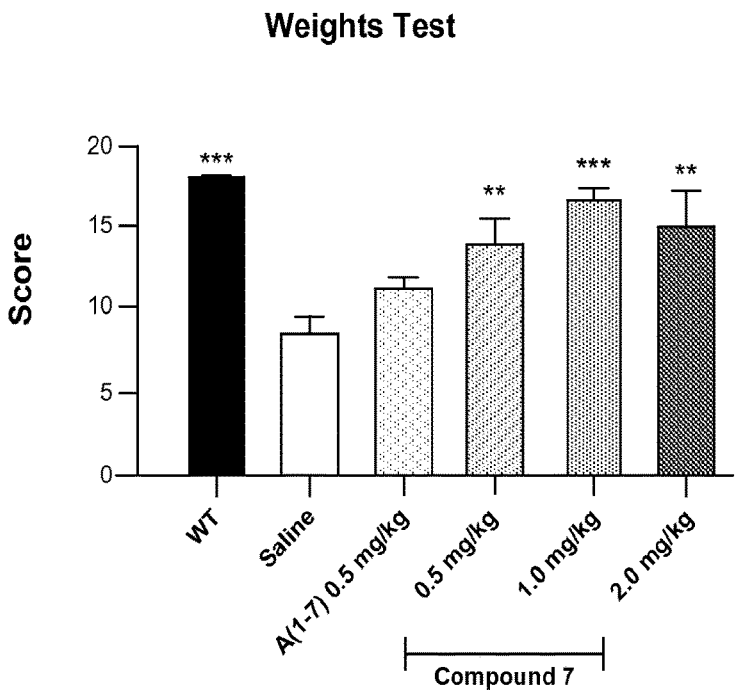
FIG. 2: Performance on the weights test and calculation of grip score [Deacon, 2013] allowed a measure of forepaw grip strength was recorded following 9 weeks of treadmill exercise (12-15 m/min 3 times per week) and treatment. Six different subcutaneously delivered treatment groups (n=6/group) were evaluated—wild-type (WT) C57BL/10SnJ control mice plus five groups of $Dmd^{mdx}$ (C57BL/10ScSn-$Dmd^{mdx}$/J) mice: vehicle (saline/Tween 20), A(1-7) 0.5 mg/kg/day, and Compound 7 at three doses (0.5, 1.0, and 2.0 mg/kg/day). Treatment of $Dmd^{mdx}$ mice with 0.5, 1.0 and 2.0 mg/kg/day of Compound 7 showed significantly (=P≤0.01; *=P≤0.001, t-test) weights test score compared to vehicle treated $Dmd^{mdx}$.

Results: In this study, the novel orally bioavailable small molecule non-peptidic Mas agonist, Compound 7, increased muscle strength by both the inverted grid test and the weights test of grip strength (FIGS. 1 and 2). In the latter test, the Mas agonist was superior to A(1-7).

Figure 4:
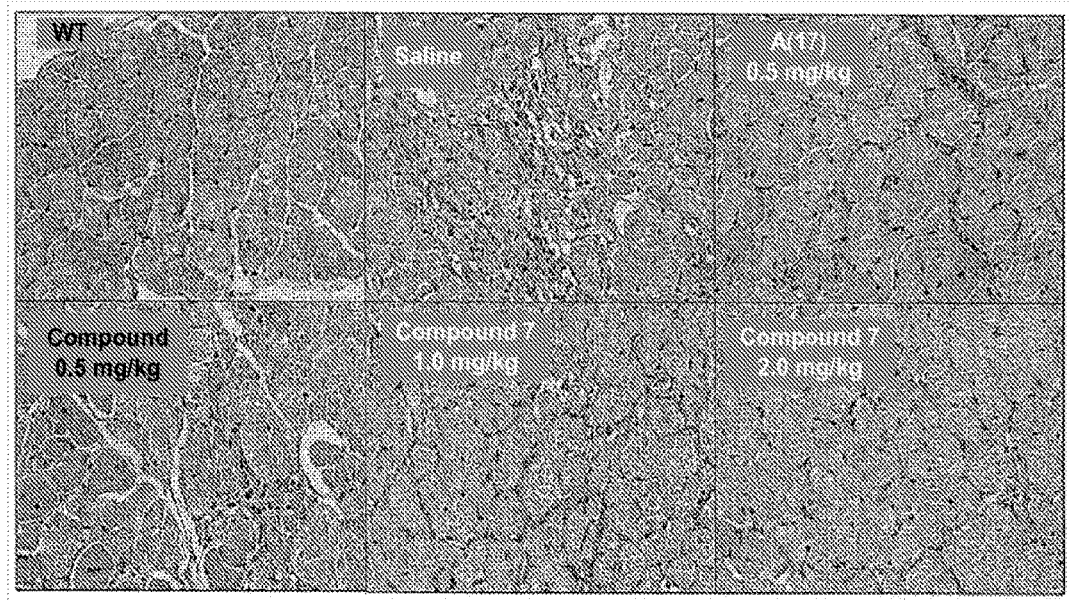
FIG. 4: Histological evaluation: Six different subcutaneously delivered treatment groups (n=6/group) were evaluated—wild-type (WT) C57BL/10SnJ control mice plus five groups of Dmd$^{mdx}$ (C57BL/10ScSn-Dmd$^{mdx}$/J) mice: vehicle (saline/Tween 20), A(1-7) 0.5 mg/kg/day, and Compound 7 at three doses (0.5, 1.0, and 2.0 mg/kg/day). At necropsy, following 9 weeks of treadmill exercise (12-15 m/min 3 times per week) and treatment, diaphragms were collected, fixed for 2 days in foramalin, paraffin embedded, sectioned, and H&E stained. Saline treated mice had significant signs of muscle atrophy, fibrosis, and inflammation when compared to WT mice and Compound 7 and A(1-7) treated mice.
Figure 5:
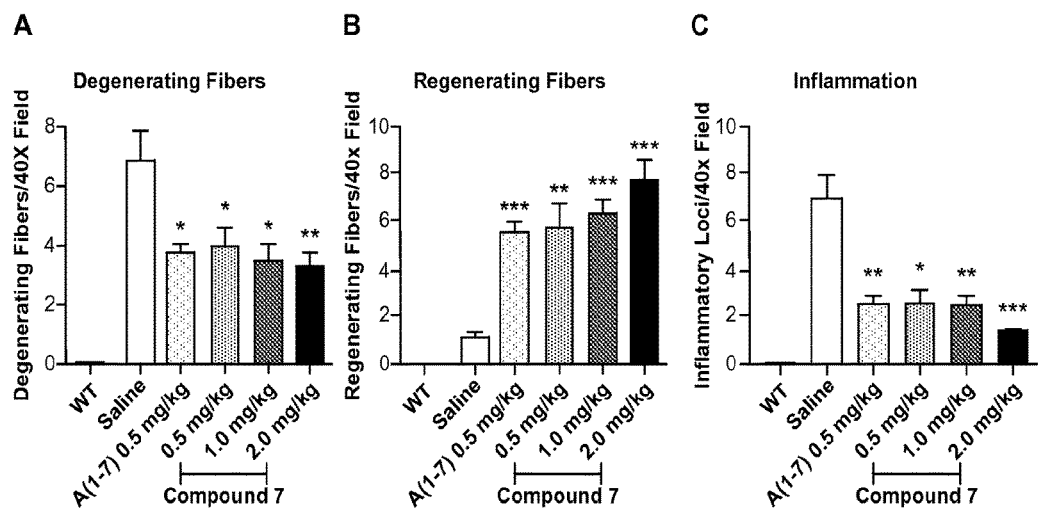
FIG. 5: Histological evaluation: H&E stained diaphragm section, prepared as described in FIG. 4, were analyzed by for degenerating and regenerating fibers as well as inflammation. For each animal (n=6 per treatment group) 5 random 40× fields were taken across the diaphragm section and analyzed. (A) Degenerating fibers were counted as deadened fibers co-localized with an open space. Compound 7 was able to reduce degenerating fibers when compared to saline treated Dmd$^{mdx}$ mice. Compound 7 across the dosage was similar to Dmd$^{mdx}$ mice treated with A(1-7). (B) The number of regenerating fibers per field were counted as healthy fibers appearing with basophilic staining. Compound 7 treated animals had significantly increased number of regenerating fibers when compared to saline treatment, and similar to A(1-7) treatment. (C) Inflammation was quantified as loci of 10 or more inflammatory cells. Compound 7 treated animals had significantly increased number of regenerating fibers when compared to saline treatment, and similar to A(1-7) treatment (*=P≤0.05; =P≤0.01; *=P≤0.001, t-test).

Histological evaluation of the diaphragm revealed a reduction in the number of degenerative fibers (increased in the mice with the mdx mutation), in $Dmd^{mdx}$ mice after treatment with Compound 7 or A(1-7) (See photomicrograph, FIG. 4, and graph in FIG. 5).

Further, consistent with the bone marrow results below, treatment with Mas agonists increased the number of regenerative fibers in the diaphragm of the $Dmd^{mdx}$ mice (FIG. 5). The basophilic fibers tended to be in clusters or areas of inflammation. Finally, treatment of $Dmd^{mdx}$ mice with Mas agonists resulted in a decrease in the number of inflammatory loci seen by histological evaluation of the diaphragm.

Figure 3:
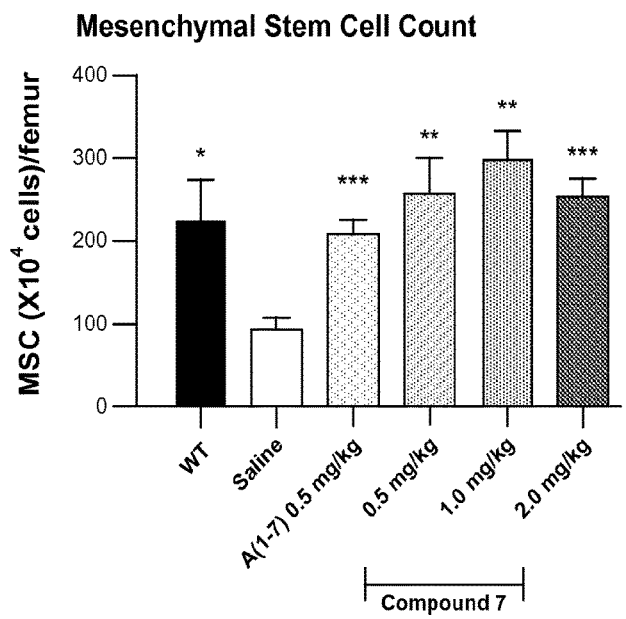
FIG. 3: Six different subcutaneously delivered treatment groups (n=6/group) were evaluated—wild-type (WT) C57BL/10SnJ control mice plus five groups of $Dmd^{mdx}$ (C57BL/10ScSn-$Dmd^{mdx}$/J) mice: vehicle (saline/Tween 20), A(1-7) 0.5 mg/kg/day, and Compound 7 at three doses (0.5, 1.0, and 2.0 mg/kg/day). At necropsy, following 9 weeks of treadmill exercise (12-15 m/min 3 times per week) and treatment, bone marrow was collected from both femurs, cultured 8 days, and mesenchymal stem cell (MSC) counts were recorded. Treatment of $Dmd^{mdx}$ mice with 0.5, 1.0 and 2.0 mg/kg/day of Compound 7 and 0.5 mg/kg of A(1-7) showed significantly (*=P≤0.05; =P≤0.01; *=P≤0.001, t-test) increased bone marrow MSC counts compared to vehicle treated $Dmd^{mdx}$.

Bone marrow analysis of the mesenchymal stem cell (MSC) populations revealed a significant increase in these cells in treated animals and, thus, points to the potential of Mas agonists to regenerate muscle through stem cell differentiation and activation (FIG. 3). Further, studies that injected MSC into animal models of muscular dystrophy showed improvement in their outcomes [Liu et al., 2007]. These cells have both a regenerative and an anti-inflammatory component.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Those skilled in the art will recognize, or be able to ascertain using no more than routine experimentation, many equivalents to the specific embodiments of the method and compositions described herein. Such equivalents are intended to be encompassed by the following claims.

REFERENCES

All references cited herein, including but not limited to patents, patent applications, and non-patent literature, are hereby incorporated by reference herein in their entirety.

Acuña, M. J., Pessina, P., Olguin, H., Cabrera, D., Vio, C. P., Bader, M., . . . & Brandan, E. (2014). Restoration of muscle strength in dystrophic muscle by angiotensin-1-7 through inhibition of TGF-β signaling. *Human Molecular Genetics*, 23(5), 1237-1249.

Brenman, J. E., Chao, D. S., Xia, H., Aldape, K., & Bredt, D. S. (1995). Nitric oxide synthase complexed with dystrophin and absent from skeletal muscle sarcolemma in Duchenne muscular dystrophy. *Cell*, 82(5), 743-752.

Brink M, Price S R, Chrast J, Bailey J L, Anwar A, Mitch W E, Delafontaine P. Angiotensin II induces skeletal muscle wasting through enhanced protein degradation and down-regulates autocrine insulin-like growth factor I. Endocrinology. 2001 April; 142(4):1489-96.

Cisternas F, Morales M G, Meneses C, Simon F, Brandan E, Abrigo J, Vazquez Y, Cabello-Verrugio C. Angiotensin-(1-7) decreases skeletal muscle atrophy induced by angiotensin II through a Mas receptor-dependent mechanism. Clin Sci (Lond). 2015 March; 128(5): 307-19.

De Luca, A., Pierno, S., Liantonio, A., Cetrone, M., Camerino, C., Fraysse, B., Mirabella, M., Servidei, S., Rüegg, U. T., & Camerino, D. C. (2003). Enhanced dystrophic progression in mdx mice by exercise and beneficial effects of taurine and insulin-like growth factor-1. *J Pharmacol Exp Ther*, 304(1), 453-463.

Deacon, R M J. Measuring the Strength of Mice. 2013, *J Vis Exp.* 2013; (76): 2610

Durik, M., Sevá Pessôa, B., & Roks, A. J. (2012). The renin-angiotensin system, bone marrow and progenitor cells. *Clin Sci* (Lond), 123(4), 205-23.

Grobe, J. L., Mecca, A. P., Lingis, M., Shenoy, V., Bolton, T. A., Machado, J. M., Speth, R. C., Raizada, M. K., & Katovich, M. J. (2007). Prevention of angiotensin II-induced cardiac remodeling by angiotensin-(1-7). *American Journal of Physiology-Heart and Circulatory Physiology*, 292(2), H736-42.

Heitsch, H. P-thienylbenzylamides as Agonists of Angiotensin-(1-7) Receptors, and Methods of Their Preparation and Use. Aventis Pharma Deutschland Gmbh, assignee. U.S. Pat. No. 6,538,144 B2. 25 Mar. 2003.

Heitsch, H., Gabriele W. 1-(p-thienylbenzyl)imidazoles as Agonists of Angiotensin (1-7) Receptors, Processes for Their Preparation, Their Use, and Pharmaceutical Preparations Comprising Them. U.S. Pat. No. 6,235,766 B1. 22 May 2001, Iwata, M., Cowling, R. T., Gurantz, D., Moore, C., Zhang, S., Yuan, J. X., & Greenberg, B. H. (2005) Angiotensin-(1-7) binds to specific receptors on cardiac fibroblasts to initiate antifibrotic and antitrophic effects. *American Journal of Physiology-Heart and Circulatory Physiology*, 289(6), H2356-63, Jarajapu, Y. P., Bhatwadekar, A. D., Caballero, S., Hazra, S., Shenoy, V., Medina, R., Kent, D., Stitt, A. W., Thut, C., Finney, E. M., Raizada, M. K., & Grant, M. B. (2013). Activation of the ACE2/angiotensin-(1-7)/Mas receptor axis enhances the reparative function of dysfunctional diabetic endothelial progenitors. Diabetes. 62(4), 1258-69.

Klingler, W., Jurkat-Rott, K., Lehmann-Horn, F., & Schleip, R. (2012). The role of fibrosis in Duchenne muscular dystrophy. *Acta Myologica*, 31(3), 184.

Liu, Y., Yan, X., Sun, Z., Chen, B., Han, Q., Li, J., Zhao, R. C. (2007). Flk-1+ adipose-derived mesenchymal stem cells differentiate into skeletal muscle satellite cells and ameliorate muscular dystrophy in mdx mice. *Stem Cells Dev*, 16(5), 695-706.

Morales M G, Olguin H, Di Capua G, Brandan E, Simon F, Cabello-Verrugio C. Endotoxin-induced skeletal muscle wasting is prevented by angiotensin (1-7) through a p38 MAPK dependent mechanism. Clin Sci (Lond). 2015 May 19.

National Institute of Neurological Disorders and Stroke (NINDS). 2013. Muscular dystrophy: Hope through research. Available online at: http://www.ninds.nih.gov/disorders/md/detail_md.htm.

Petrof, B. J., Shrager, J. B., Stedman, H. H., Kelly, A. M., & Sweeney, H. L. (1993). Dystrophin protects the sarcolemma from stresses developed during muscle contraction. *Proc Natl Acad Sci USA*, 90(8), 3710-3714.

Sabharwal, R., Cicha, M. Z., Sinisterra, R. D., De Sousa, F. B., Santos, R. A., & Chapleau, M. W. (2014). Chronic oral administration of Ang-(1-7) improves skeletal muscle, autonomic and locomotor phenotypes in muscular dystrophy. Clin Sci (Lond). 2014 July; 127(2):101-9.

Sukhanov S, Semprun-Prieto L, Yoshida T, Michael Tabony A, Higashi Y, Galvez S, Delafontaine P. Angiotensin II, oxidative stress and skeletal muscle wasting. Am J Med Sci. 2011 August; 342(2):143-7.

Wilton, S. D., & Fletcher, S. (2011). Novel compounds for the treatment of Duchenne muscular dystrophy: emerging therapeutic agents. *Appl Clin Genet*, 4, 29.

What is claimed is:

1. A method of treating a subject with a musculoskeletal disease, a muscle dysfunction or muscle-wasting disease or disorder, comprising: administering to the subject in need thereof an effective amount of a compound having the general formula 1, or a salt thereof:

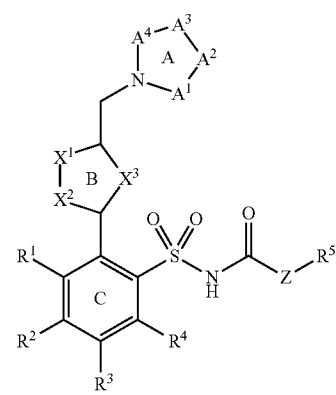

wherein:
ring A is a five-membered or six-membered heteroaryl or heterocyclyl ring containing either a combination of two non-adjacent nitrogen or oxygen atoms, or a combination of three or four nitrogen or oxygen atoms;
ring B is a five-membered or six-membered heteroaryl ring that contains at least one nitrogen atom;
ring C is an optionally substituted aryl ring;
$A^1$, $A^2$, $A^3$, $A^4$ are independently selected from a group consisting of =N—, —C(=O)—, —C($R^a$)=, =C($R^b$)—, —C($R^c$)($R^d$)—N($R^e$)—, —C($R^c$)($R^d$)—O—, or —[C($R^c$)($R^d$)]$_n$— with n being 1 or 2;
$X^1$—$X^2$ is ($R^6$)C—N, N—C(R6), N—N, N—O, O—N, N—S or S—N;
$X^3$ is ($R^7$)C=C($R^8$), O, S, or N($R^9$);
Z is O, NH or a bond to $R^5$;
$R^a$ and $R^b$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^a$ and $R^b$ can also join to form a ring of up to 6 atoms;
$R^c$ and $R^d$ are independently selected from a group consisting of hydrogen, alkyl, aryl, or heteroaryl, provided that $R^c$ and $R^d$ can also join to form a ring of up to 6 atoms;
$R^e$ is hydrogen, alkyl, aryl, heteroaryl, acyl, alkoxyacyl, aminoacyl, dialkylaminoacyl, or dialkylaminoacyl;
$R^1$, $R^3$, $R^4$, $R^6$, $R^7$, and $R^8$ are independently selected from a group consisting of hydrogen, alkyl, alkenyl, alkynyl, aryl, heteroaryl, arylmethyl, heteroarylmethyl, fluoro, chloro, bromo, iodo, cyano, hydroxy, amino, alkylamino, alkoxy, aryloxy, alkoxyalkyl, or aryloxyalkyl;

$R^2$ is alkyl, alkenyl, alkynyl, aryl, heteroaryl, arylmethyl, heteroarylmethyl, alkoxy, trifluoromethoxy, perfluoroalkoxy, aryloxy, alkoxyalkyl, or aryloxyalkyl;

$R^5$ is alkyl, aryl, heteroaryl, hydroxyalkyl, carboxyalkyl, alkoxyalkyl, or aryloxyalkyl; and $R^9$ is hydrogen, alkyl, aryl, heteroaryl, acyl, alkoxyacyl, aminoacyl, dialkylaminoacyl, or dialkylaminoacyl.

2. The method of claim 1, wherein ring A is selected from the group consisting of:

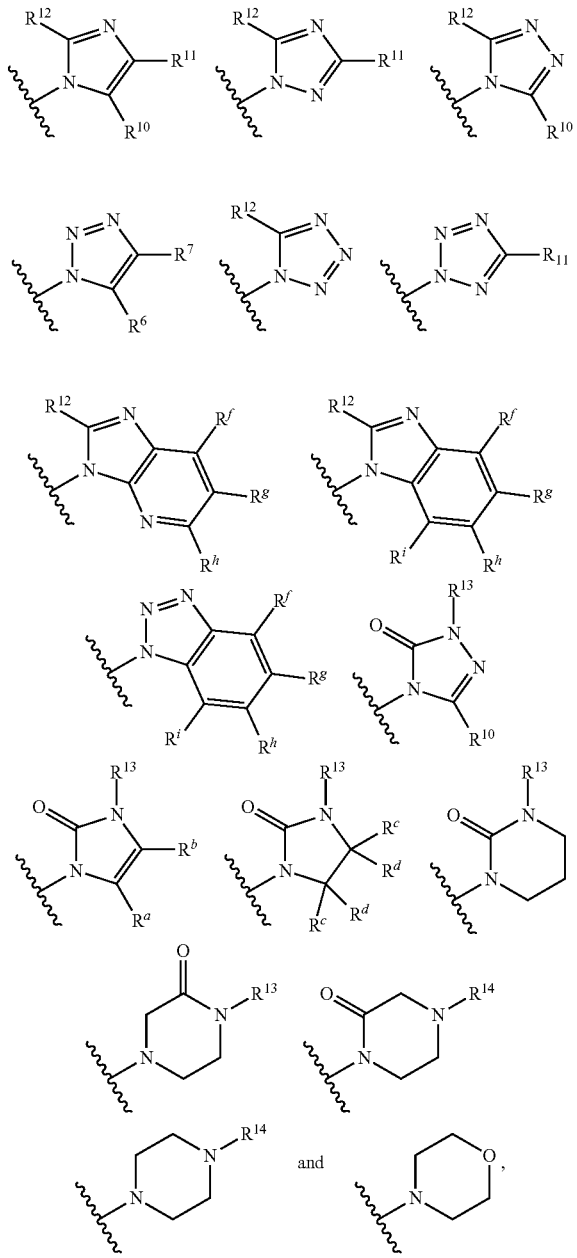

wherein:
$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or heteroaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{13}$ is hydrogen, alkyl, aryl, or heteroaryl;

$R^{14}$ is hydrogen, alkyl, aryl, heteroaryl, acyl, alkoxyacyl, aminoacyl, dialkylaminoacyl, or dialkylaminoacyl; and $R^f$, $R^g$, $R^h$, and $R^i$, are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, or aryloxyalkyl.

3. The method of claim 1, wherein ring B is selected from the group consisting of:

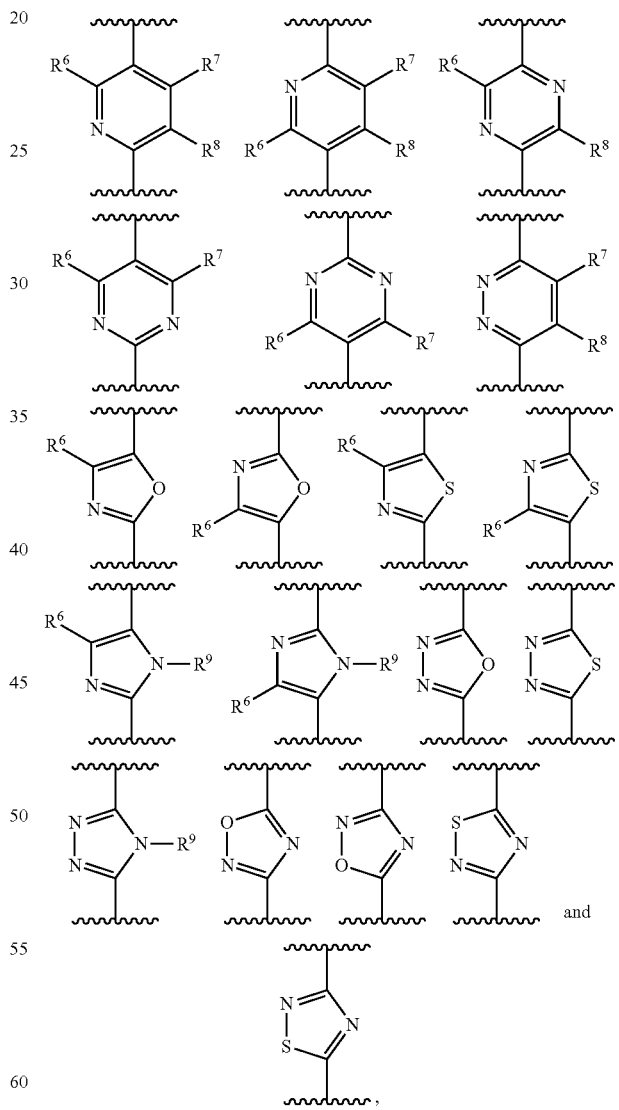

wherein groups $R^6$, $R^7$, $R^8$ and $R^9$ are defined as in general formula 1.

4. The method of claim 1, wherein the compound is selected from the group consisting of:

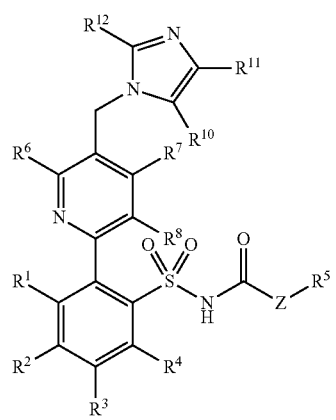
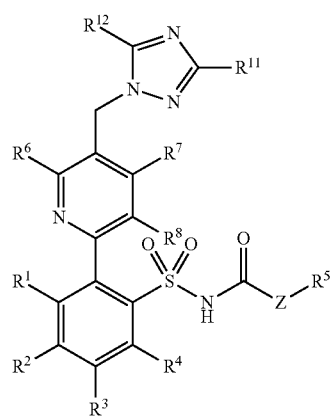
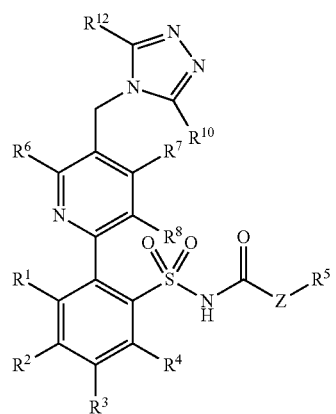
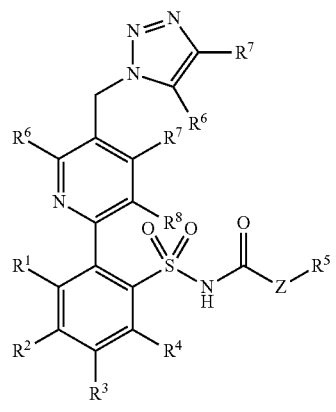
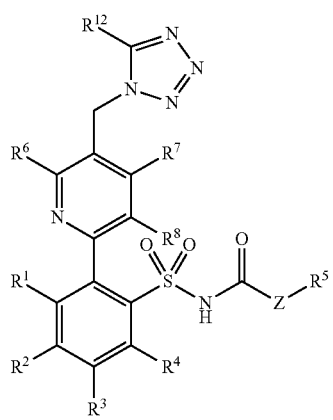
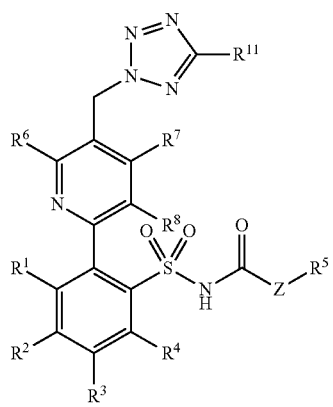
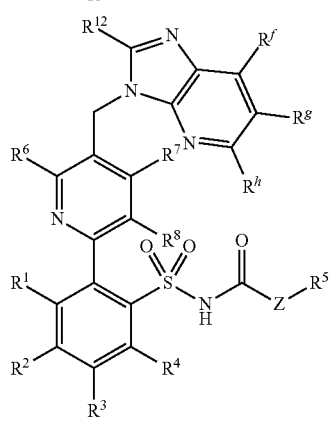
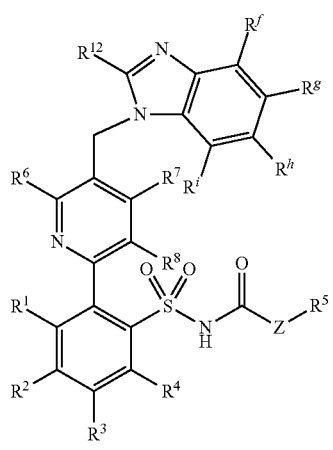

49
-continued
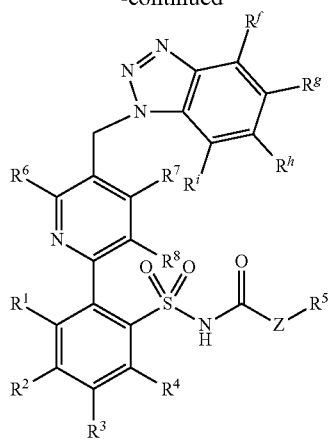
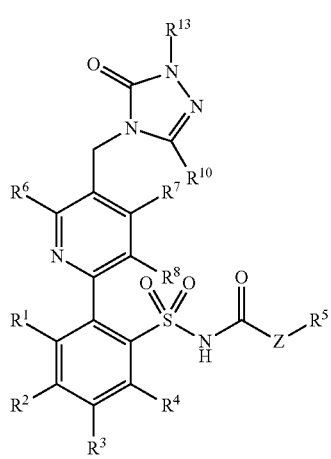
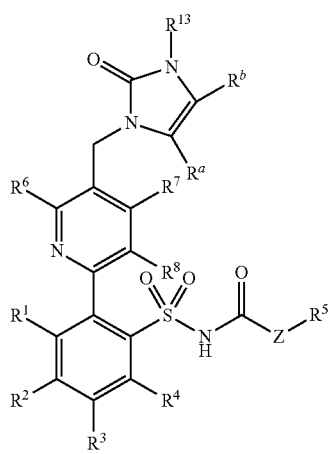
50
-continued
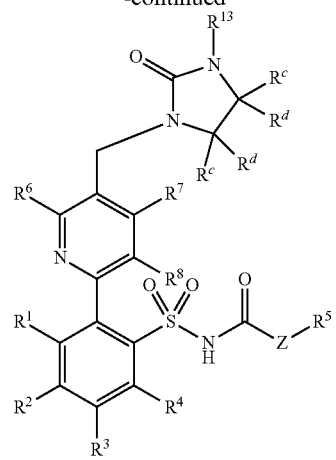
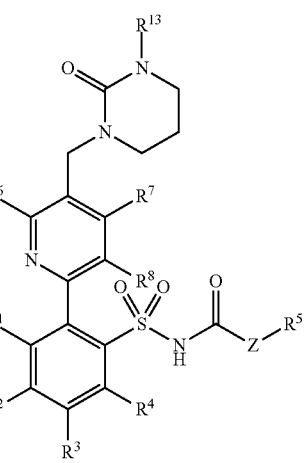
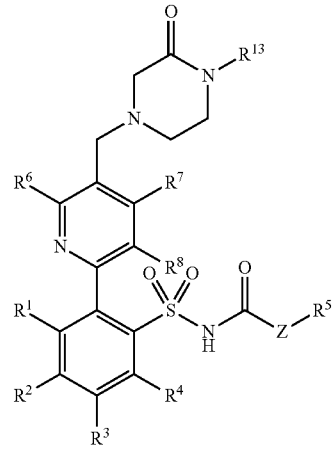

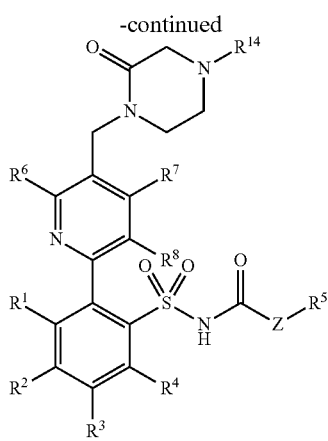

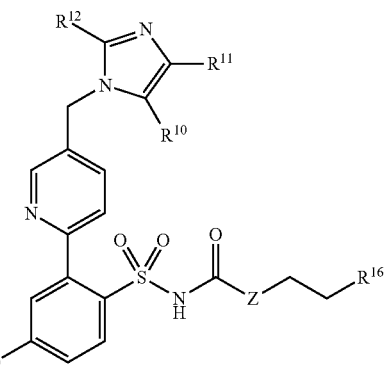

boxy, provided that $R^{10}$ and $R^{11}$ can also be joined to form a carbocyclic, heterocyclic, aryl or heteroaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{13}$ is hydrogen, alkyl, aryl or heteroaryl;

$R^{14}$ is hydrogen, alkyl, aryl, heteroaryl, acyl, alkoxyacyl, aminoacyl, dialkylaminoacyl, or dialkylaminoacyl; and $R^f$, $R^g$, $R^h$, and $R^i$, are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, or aryloxyalkyl.

5. The method of claim 1, wherein $R^2$ is trifluoromethoxy.

6. The method of claim 1, wherein Z is O or NH.

7. The method of claim 1, wherein the compound has the general formula 4a:

wherein:

Z is O or NH $R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or heteroaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{15}$ is alkyl, aryl, heteroaryl, arylmethyl, heteroarylmethyl, trifluoromethyl or pentafluoroethyl; and $R^{16}$ is hydrogen, hydroxy, methoxy, alkoxy, alkyl, alkenyl, alkynyl, aryl, heteroaryl, amino, alkylamino, or dialkylamino.

8. The method of claim 1, wherein the compound has the general formula 4a:

wherein:

$R^1$, $R^2$, $R^3$, $R^4$, $R^5$, $R^6$, $R^7$, $R^8$, $R^9$, $R^a$, $R^b$, $R^c$, $R^d$ and Z are defined as in general formula 1, $R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or car-

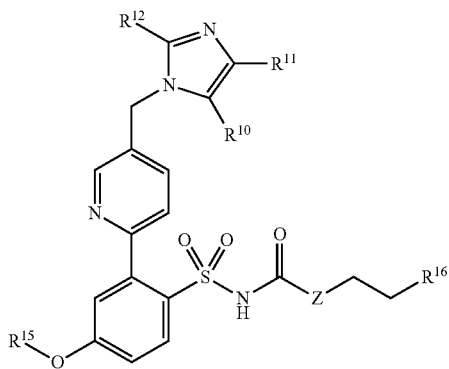

wherein:
Z is O or NH
$R^{10}$, $R^{11}$ and $R^{12}$ are hydrogen;
$R^{15}$ is alkyl, aryl, heteroaryl, arylmethyl, heteroarylmethyl, hifluoromethyl or pentafluoroethyl; and
$R^{16}$ is hydrogen, hydroxy, methoxy, alkoxy, alkyl, alkenyl, alkynyl, aryl, heteroaryl, amino, alkylamino, or dialkylamino.

9. The method of claim 1, wherein the compound has the general formula 4a:

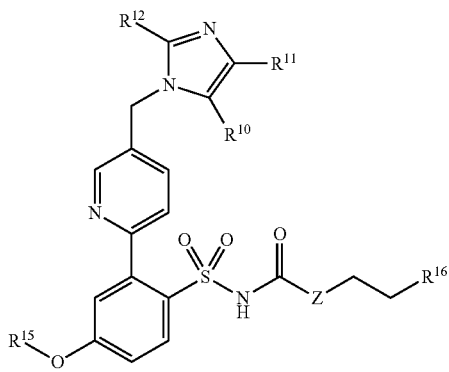

wherein:
Z is O or NH
$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or heteroaryl ring;
$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;
$R^{15}$ is trifluoromethyl and $R^{16}$ is ethyl.

10. The method of claim 1, wherein the compound has the formula 7, or a salt thereof

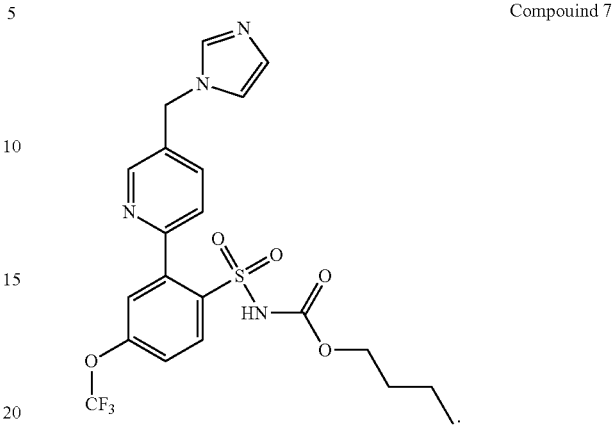

Compouind 7

11. The method of claim 1, wherein the amount of the provided compound is effective to ameliorate at least one symptom associated with a muscle-wasting disease, or to postpone or prevent the onset of at least one symptom of the disease.

12. The method of claim 1, wherein the musculoskeletal disease, muscle dysfunction or muscle-wasting disease or disorder is a hereditary myopathy or neuromuscular disease involving joint or skeletal deformities selected from a group consisting of muscular dystrophy, muscle atrophy, X-linked spinal-bulbar muscular atrophy, Duchenne muscular dystrophy, Becker muscular dystrophy, limb-girdle muscular dystrophy, facioscapulhumeral muscular dystrophy, congenital muscular dystrophy, oculopharyngeal muscular dystrophy, distal muscular dystrophy, myotonic dystrophy, and Emery-Dreifuss muscular dystrophy.

13. The method of claim 1, wherein the muscle-wasting disease is muscular dystrophy.

14. The method of claim 1, wherein the muscle-wasting disease is Duchenne muscular dystrophy.

15. The method of claim 1, wherein the muscle-wasting disease is limb-girdle muscular dystrophy.

16. The method of claim 1, wherein the muscle-wasting disease is drug-induced myopathy.

17. The method of claim 1, wherein the provided compound or pharmaceutically acceptable salt thereof is provided as a composition comprising the compound or pharmaceutically acceptable salt thereof and a pharmaceutically acceptable carrier suitable for oral, parenteral, or topical administration.

18. The method of claim 1, wherein the musculoskeletal disease, muscle dysfunction or muscle-wasting disease or disorder comprises hereditary myopathy, neuromuscular disease, muscular dystrophy, muscular atrophy, drug-induced myopathy, or an illness, disease, disorder or condition that causes a decrease in muscle strength.

* * * * *